(12) United States Patent
Schmidt et al.

(10) Patent No.: US 9,492,674 B2
(45) Date of Patent: Nov. 15, 2016

(54) LEADLESS CARDIAC PACEMAKER WITH DELIVERY AND/OR RETRIEVAL FEATURES

(71) Applicant: Cardiac Pacemakers, Inc., St. Paul, MN (US)

(72) Inventors: Brian L. Schmidt, White Bear Lake, MN (US); Benjamin J. Haasl, Forest Lake, MN (US); Keith R. Maile, New Brighton, MN (US); Dana Sachs, Pine City, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 191 days.

(21) Appl. No.: 14/451,601

(22) Filed: Aug. 5, 2014

(65) Prior Publication Data
US 2015/0051611 A1 Feb. 19, 2015

Related U.S. Application Data

(60) Provisional application No. 61/866,644, filed on Aug. 16, 2013.

(51) Int. Cl.
| | | |
|---|---|---|
| *A61B 19/00* | (2006.01) | |
| *A61N 1/375* | (2006.01) | |
| *A61N 1/362* | (2006.01) | |
| *A61N 1/372* | (2006.01) | |

(52) U.S. Cl.
CPC ............ *A61N 1/3756* (2013.01); *A61N 1/362* (2013.01); *A61N 1/37205* (2013.01)

(58) Field of Classification Search
CPC ........... A61N 1/3756; A61N 1/37205; A61N 1/362; A61N 2001/0578; A61N 1/0573; A61N 1/059; A61N 1/372; A61N 2001/058; A61N 1/057; A61N 1/0587; A61B 5/0215; A61B 2017/22035; A61B 17/221; A61B 5/686; A61F 2002/011; A61F 2/2427
USPC ................ 600/373; 606/128, 129, 200, 108; 607/122, 126, 127, 128; 623/1.11
See application file for complete search history.

(56) References Cited

U.S. PATENT DOCUMENTS

| | | |
|---|---|---|
| 721,869 A | 3/1903 | Dunning |
| 3,717,151 A | 2/1973 | Collett |
| 3,754,555 A | 8/1973 | Schmitt |
| 3,814,104 A | 6/1974 | Irnich et al. |

(Continued)

FOREIGN PATENT DOCUMENTS

| | | |
|---|---|---|
| CA | 1003904 A1 | 1/1977 |
| DE | 2053919 A1 | 5/1972 |

(Continued)

OTHER PUBLICATIONS

Spickler, et al. "Totally Self-Contained Intracardiac Pacemaker" J. Electrocardiology, vol. 3, Nos. 3 & 4, pp. 325-331 (1970).

*Primary Examiner* — Katherine M Shi
(74) *Attorney, Agent, or Firm* — Seager, Tufte & Wickhem LLP

(57) ABSTRACT

An implantable leadless cardiac pacing device and associated delivery and retrieval devices. The implantable device includes a docking member extending from the proximal end of the housing of the implantable device configured to engage with the delivery and/or retrieval device to facilitate delivery and/or retrieval of the implantable leadless cardiac pacing device.

12 Claims, 49 Drawing Sheets

(56) References Cited

U.S. PATENT DOCUMENTS

| | | |
|---|---|---|
| 3,835,864 A | 9/1974 | Rasor et al. |
| 3,902,501 A | 9/1975 | Citron et al. |
| 3,943,936 A | 3/1976 | Rasor |
| 3,971,364 A | 7/1976 | Fletcher et al. |
| 3,976,082 A | 8/1976 | Schmitt |
| 4,103,690 A | 8/1978 | Harris |
| 4,112,952 A | 9/1978 | Thomas et al. |
| 4,269,198 A | 5/1981 | Stokes |
| 4,280,512 A | 7/1981 | Karr |
| 4,301,815 A | 11/1981 | Doring |
| 4,402,328 A | 9/1983 | Doring |
| 4,409,994 A | 10/1983 | Doring |
| 4,502,492 A | 3/1985 | Bornzin |
| 4,662,382 A | 5/1987 | Sluetz et al. |
| 4,898,577 A | 2/1990 | Badger et al. |
| 4,913,164 A | 4/1990 | Greene et al. |
| 5,003,990 A | 4/1991 | Osypka |
| 5,057,114 A | 10/1991 | Wittich et al. |
| 5,129,749 A | 7/1992 | Sato |
| 5,171,233 A | 12/1992 | Amplatz et al. |
| 5,193,540 A | 3/1993 | Schulman et al. |
| 5,257,634 A | 11/1993 | Kroll |
| 5,282,845 A | 2/1994 | Bush et al. |
| 5,300,107 A | 4/1994 | Stokes et al. |
| 5,318,528 A | 6/1994 | Heaven et al. |
| 5,336,253 A | 8/1994 | Gordon et al. |
| 5,405,367 A | 4/1995 | Schulman et al. |
| 5,405,374 A | 4/1995 | Stein |
| 5,411,535 A | 5/1995 | Fujii et al. |
| 5,425,756 A | 6/1995 | Heil et al. |
| 5,443,492 A | 8/1995 | Stokes et al. |
| 5,492,119 A | 2/1996 | Abrams |
| 5,522,875 A | 6/1996 | Gates et al. |
| 5,522,876 A | 6/1996 | Rusink |
| 5,545,201 A | 8/1996 | Helland et al. |
| 5,545,206 A | 8/1996 | Carson |
| 5,562,723 A | 10/1996 | Rugland et al. |
| 5,575,814 A | 11/1996 | Giele et al. |
| 5,578,068 A | 11/1996 | Laske et al. |
| 5,697,936 A | 12/1997 | Shipko et al. |
| 5,716,390 A | 2/1998 | Li |
| 5,716,391 A | 2/1998 | Grandjean |
| 5,755,764 A | 5/1998 | Schroeppel |
| 5,776,178 A | 7/1998 | Pohndorf et al. |
| 5,807,399 A | 9/1998 | Laske et al. |
| 5,837,006 A | 11/1998 | Ocel et al. |
| 5,837,007 A | 11/1998 | Altman et al. |
| 5,851,226 A | 12/1998 | Skubitz et al. |
| 5,871,531 A | 2/1999 | Struble |
| 5,908,381 A | 6/1999 | Aznoian et al. |
| 5,908,447 A | 6/1999 | Schroeppel et al. |
| 6,041,258 A | 3/2000 | Cigaina et al. |
| 6,055,457 A | 4/2000 | Bonner |
| 6,074,401 A | 6/2000 | Gardiner et al. |
| 6,078,840 A | 6/2000 | Stokes |
| 6,093,177 A | 7/2000 | Javier et al. |
| 6,129,749 A | 10/2000 | Bartig et al. |
| 6,132,456 A | 10/2000 | Sommer et al. |
| 6,181,973 B1 | 1/2001 | Ceron et al. |
| 6,188,932 B1 | 2/2001 | Lindegren |
| 6,240,322 B1 | 5/2001 | Peterfeso et al. |
| 6,251,104 B1 | 6/2001 | Kesten et al. |
| 6,290,719 B1 | 9/2001 | Garberoglio |
| 6,321,124 B1 | 11/2001 | Cigaina |
| 6,322,548 B1 | 11/2001 | Payne et al. |
| RE37,463 E | 12/2001 | Altman |
| 6,358,256 B1 | 3/2002 | Reinhardt |
| 6,363,938 B2 | 4/2002 | Saadat et al. |
| 6,381,495 B1 | 4/2002 | Jenkins |
| 6,381,500 B1 | 4/2002 | Fischer, Sr. |
| 6,408,214 B1 | 6/2002 | Williams et al. |
| 6,458,145 B1 | 10/2002 | Ravenscroft et al. |
| 6,477,423 B1 | 11/2002 | Jenkins |
| 6,500,182 B2 | 12/2002 | Foster |
| 6,510,332 B1 | 1/2003 | Greenstein |
| 6,510,345 B1 | 1/2003 | Van Bentem |
| 6,522,915 B1 | 2/2003 | Ceballos et al. |
| 6,572,587 B2 | 6/2003 | Lerman et al. |
| 6,582,441 B1 | 6/2003 | He et al. |
| 6,592,581 B2 | 7/2003 | Bowe |
| 6,623,518 B2 | 9/2003 | Thompson et al. |
| 6,626,915 B2 | 9/2003 | Leveillee |
| 6,638,268 B2 | 10/2003 | Niazi |
| 6,684,109 B1 | 1/2004 | Osypka |
| 6,711,443 B2 | 3/2004 | Osypka |
| 6,743,240 B2 | 6/2004 | Smith et al. |
| 6,755,812 B2 | 6/2004 | Peterson et al. |
| 6,909,920 B2 | 6/2005 | Lokhoff et al. |
| 6,944,507 B2 | 9/2005 | Fröberg et al. |
| 6,953,454 B2 | 10/2005 | Peterson et al. |
| 7,027,876 B2 | 4/2006 | Casavant et al. |
| 7,082,335 B2 | 7/2006 | Klein et al. |
| 7,085,606 B2 | 8/2006 | Flach et al. |
| 7,092,765 B2 | 8/2006 | Geske et al. |
| 7,092,766 B1 | 8/2006 | Salys et al. |
| 7,120,504 B2 | 10/2006 | Osypka |
| 7,149,587 B2 | 12/2006 | Wardle et al. |
| 7,158,838 B2 | 1/2007 | Seifert et al. |
| 7,162,310 B2 | 1/2007 | Doan |
| 7,181,288 B1 | 2/2007 | Rezai et al. |
| 7,187,982 B2 | 3/2007 | Seifert et al. |
| 7,200,437 B1 | 4/2007 | Nabutovsky et al. |
| 7,212,869 B2 | 5/2007 | Wahlstrom et al. |
| 7,229,415 B2 | 6/2007 | Schwartz |
| 7,251,532 B2 | 7/2007 | Hess et al. |
| 7,289,853 B1 | 10/2007 | Campbell et al. |
| 7,313,445 B2 | 12/2007 | McVenes et al. |
| 7,326,231 B2 | 2/2008 | Phillips et al. |
| 7,328,071 B1 | 2/2008 | Stehr et al. |
| 7,383,091 B1 | 6/2008 | Chitre et al. |
| 7,450,999 B1 | 11/2008 | Karicherla et al. |
| 7,462,184 B2 | 12/2008 | Worley et al. |
| 7,463,933 B2 | 12/2008 | Wahlstrom et al. |
| 7,499,758 B2 | 3/2009 | Cates et al. |
| 7,509,169 B2 | 3/2009 | Eigler et al. |
| 7,515,971 B1 | 4/2009 | Doan |
| 7,532,939 B2 | 5/2009 | Sommer et al. |
| 7,558,631 B2 | 7/2009 | Cowan et al. |
| 7,634,319 B2 | 12/2009 | Schneider et al. |
| 7,647,109 B2 | 1/2010 | Hastings et al. |
| 7,657,325 B2 | 2/2010 | Williams |
| 7,678,128 B2 | 3/2010 | Boyle et al. |
| 7,717,899 B2 | 5/2010 | Bowe et al. |
| 7,731,655 B2 | 6/2010 | Smith et al. |
| 7,734,343 B2 | 6/2010 | Ransbury et al. |
| 7,740,640 B2 | 6/2010 | Ginn |
| 7,785,264 B2 | 8/2010 | Hettrick et al. |
| 7,799,037 B1 | 9/2010 | He et al. |
| 7,801,624 B1 | 9/2010 | Flannery et al. |
| 7,835,801 B1 | 11/2010 | Sundararajan et al. |
| 7,840,281 B2 | 11/2010 | Kveen et al. |
| 7,840,283 B1 | 11/2010 | Bush et al. |
| 7,860,580 B2 | 12/2010 | Falk et al. |
| 7,875,049 B2 | 1/2011 | Eversull et al. |
| 7,890,186 B2 | 2/2011 | Wardle et al. |
| 7,904,179 B2 | 3/2011 | Rutten et al. |
| 7,920,928 B1 | 4/2011 | Yang et al. |
| 7,993,351 B2 | 8/2011 | Worley et al. |
| 8,010,209 B2 | 8/2011 | Jacobson |
| 8,036,757 B2 | 10/2011 | Worley |
| 8,057,486 B2 | 11/2011 | Hansen |
| 8,082,035 B2 | 12/2011 | Glukhovsky |
| 8,103,361 B2 | 1/2012 | Moser |
| 8,108,054 B2 | 1/2012 | Helland |
| 8,142,347 B2 | 3/2012 | Griego et al. |
| 8,160,722 B2 | 4/2012 | Rutten et al. |
| 8,185,213 B2 | 5/2012 | Kveen et al. |
| 8,219,213 B2 | 7/2012 | Sommer et al. |
| 8,233,994 B2 | 7/2012 | Sommer et al. |
| 8,252,019 B2 | 8/2012 | Fleming, III |
| 8,295,939 B2 | 10/2012 | Jacobson |
| 8,313,445 B2 | 11/2012 | Mishima et al. |
| 8,352,025 B2 | 1/2013 | Jacobson |
| 8,352,028 B2 | 1/2013 | Wenger |

(56) References Cited

U.S. PATENT DOCUMENTS

| | | |
|---|---|---|
| 8,364,277 B2 | 1/2013 | Glukhovsky |
| 8,364,280 B2 | 1/2013 | Marnfeldt et al. |
| 8,406,900 B2 | 3/2013 | Barlov et al. |
| 8,406,901 B2 | 3/2013 | Starkebaum et al. |
| 8,428,750 B2 | 4/2013 | Kolberg |
| 8,452,420 B2 | 5/2013 | Flach et al. |
| 8,478,431 B2 | 7/2013 | Griswold et al. |
| 8,489,189 B2 | 7/2013 | Tronnes |
| 8,494,650 B2 | 7/2013 | Glukhovsky et al. |
| 8,504,156 B2 | 8/2013 | Bonner et al. |
| 8,518,060 B2 | 8/2013 | Jelich et al. |
| 8,527,068 B2 | 9/2013 | Ostroff |
| 8,532,790 B2 | 9/2013 | Griswold |
| 8,548,605 B2 | 10/2013 | Ollivier |
| 8,565,897 B2 | 10/2013 | Regnier et al. |
| 8,615,310 B2 | 12/2013 | Khairkhahan et al. |
| 8,634,912 B2 | 1/2014 | Bornzin et al. |
| 8,670,842 B1 | 3/2014 | Bornzin et al. |
| 8,721,587 B2 | 5/2014 | Berthiaume et al. |
| 8,727,996 B2 | 5/2014 | Allan et al. |
| 8,758,365 B2 | 6/2014 | Bonner et al. |
| 2002/0077556 A1 | 6/2002 | Schwartz |
| 2003/0004537 A1 | 1/2003 | Boyle et al. |
| 2004/0176797 A1 | 9/2004 | Opolski |
| 2005/0090890 A1 | 4/2005 | Wu et al. |
| 2005/0267555 A1 | 12/2005 | Marnfeldt et al. |
| 2006/0247753 A1 | 11/2006 | Wenger et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0233218 A1 | 10/2007 | Kolberg |
| 2007/0239248 A1 | 10/2007 | Hastings et al. |
| 2007/0255376 A1 | 11/2007 | Michels et al. |
| 2007/0276444 A1 | 11/2007 | Gelbart |
| 2007/0293904 A1 | 12/2007 | Gelbart |
| 2008/0021532 A1 | 1/2008 | Kveen et al. |
| 2009/0082828 A1 | 3/2009 | Ostroff |
| 2009/0281605 A1 | 11/2009 | Marnfeldt et al. |
| 2010/0198288 A1 | 8/2010 | Ostroff |
| 2011/0034939 A1 | 2/2011 | Kveen et al. |
| 2011/0112548 A1 | 5/2011 | Fifer et al. |
| 2011/0125163 A1 | 5/2011 | Rutten et al. |
| 2011/0190785 A1 | 8/2011 | Gerber et al. |
| 2011/0190786 A1 | 8/2011 | Gerber et al. |
| 2011/0208260 A1 | 8/2011 | Jacobson |
| 2011/0237967 A1 | 9/2011 | Moore et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0307043 A1 | 12/2011 | Ollivier |
| 2012/0078322 A1 | 3/2012 | Dal Molin et al. |
| 2012/0078336 A1 | 3/2012 | Helland |
| 2012/0095539 A1 | 4/2012 | Khairkhahan et al. |
| 2012/0109002 A1 | 5/2012 | Mothilal et al. |
| 2012/0109079 A1 | 5/2012 | Asleson et al. |
| 2012/0109148 A1 | 5/2012 | Bonner et al. |
| 2012/0109149 A1 | 5/2012 | Bonner et al. |
| 2012/0116489 A1 | 5/2012 | Khairkhahan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0197373 A1 | 8/2012 | Khairkhahan et al. |
| 2012/0232565 A1 | 9/2012 | Kveen et al. |
| 2012/0271134 A1 | 10/2012 | Allan et al. |
| 2012/0330392 A1 | 12/2012 | Regnier et al. |
| 2013/0006261 A1 | 1/2013 | Lampropoulos et al. |
| 2013/0006262 A1 | 1/2013 | Lampropoulos et al. |
| 2013/0012925 A1 | 1/2013 | Berthiaume et al. |
| 2013/0035636 A1 | 2/2013 | Beasley et al. |
| 2013/0035748 A1 | 2/2013 | Bonner et al. |
| 2013/0053921 A1 | 2/2013 | Bonner et al. |
| 2013/0079798 A1 | 3/2013 | Tran et al. |
| 2013/0079861 A1 | 3/2013 | Reinert et al. |
| 2013/0096672 A1* | 4/2013 | Reich .................. A61F 2/2466 623/2.11 |
| 2013/0103047 A1 | 4/2013 | Steingisser et al. |
| 2013/0103049 A1 | 4/2013 | Bonde |
| 2013/0116741 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0296957 A1 | 11/2013 | Tronnes |
| 2014/0058494 A1 | 2/2014 | Ostroff et al. |
| 2014/0074114 A1 | 3/2014 | Khairkhahan et al. |
| 2014/0148815 A1 | 5/2014 | Wenzel et al. |
| 2014/0180306 A1 | 6/2014 | Grubac et al. |

FOREIGN PATENT DOCUMENTS

| | | |
|---|---|---|
| EP | 779080 B1 | 5/2003 |
| JP | 05245215 A | 9/1993 |
| WO | 03032807 A2 | 4/2003 |
| WO | 2009039400 A1 | 3/2009 |
| WO | 2012092067 A1 | 7/2012 |
| WO | 2012092074 A1 | 7/2012 |

* cited by examiner

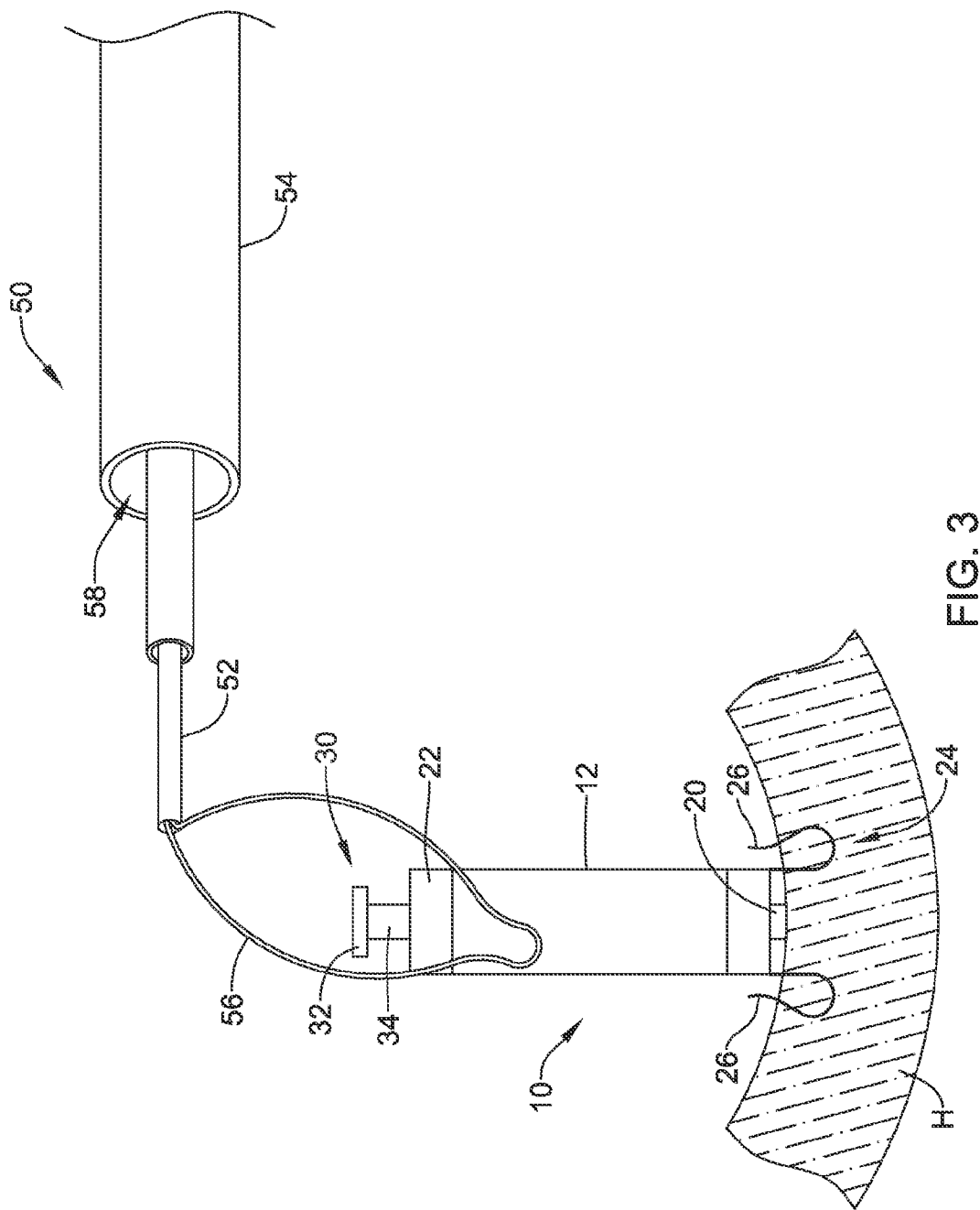

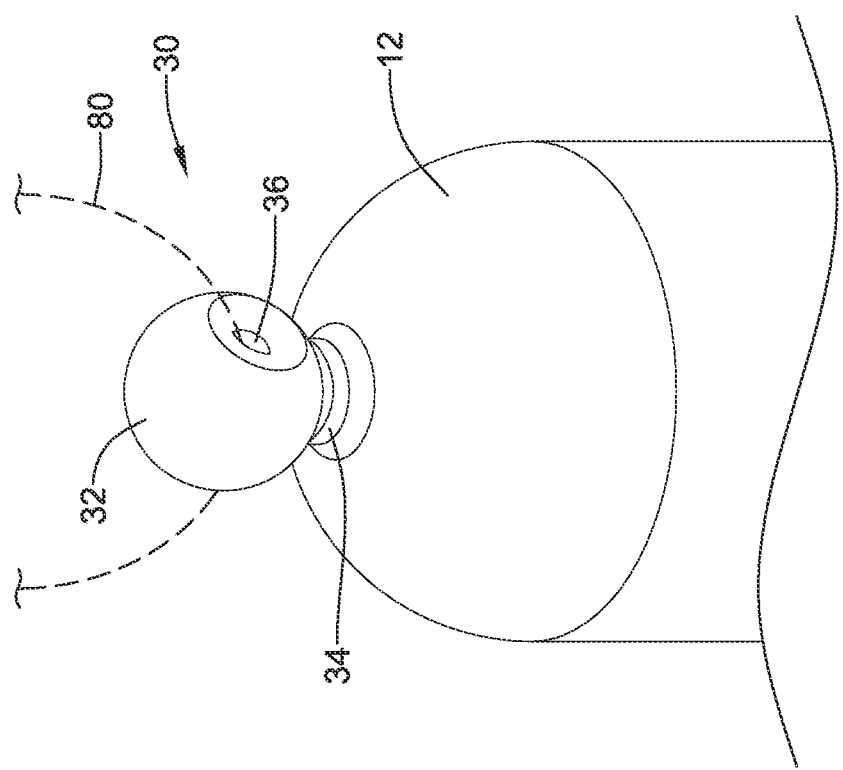

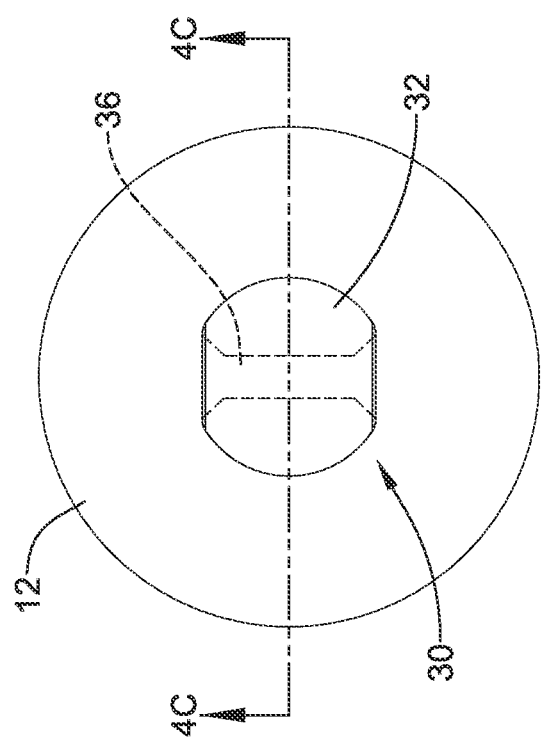

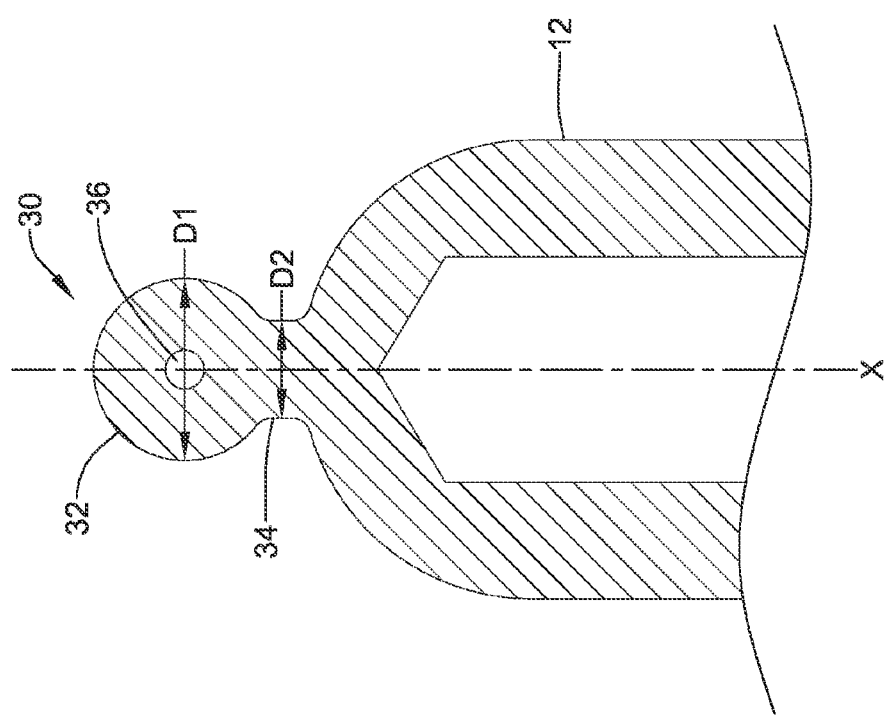

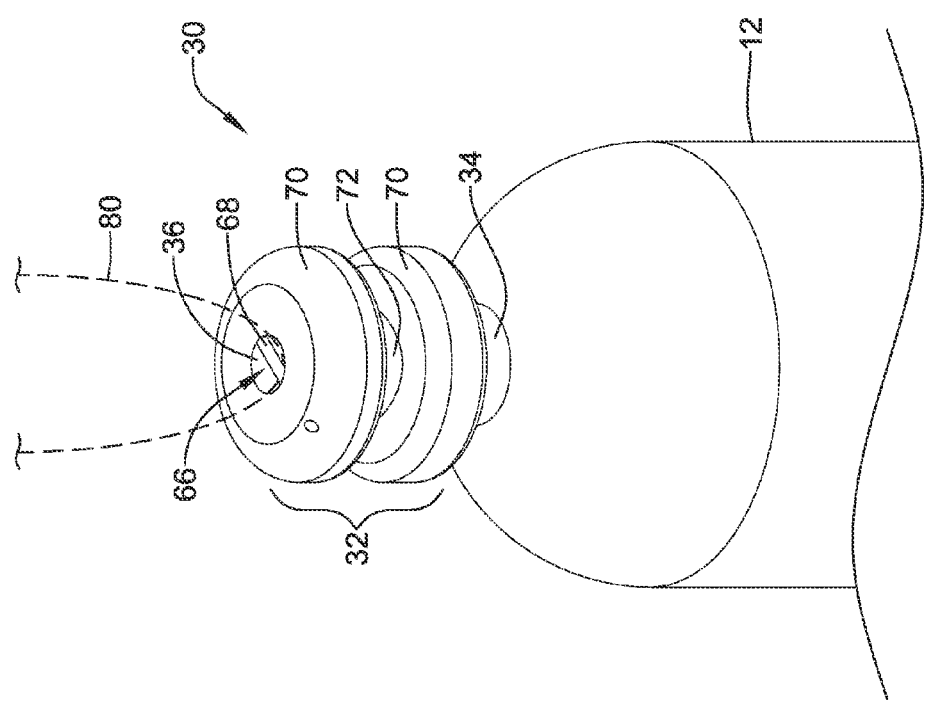

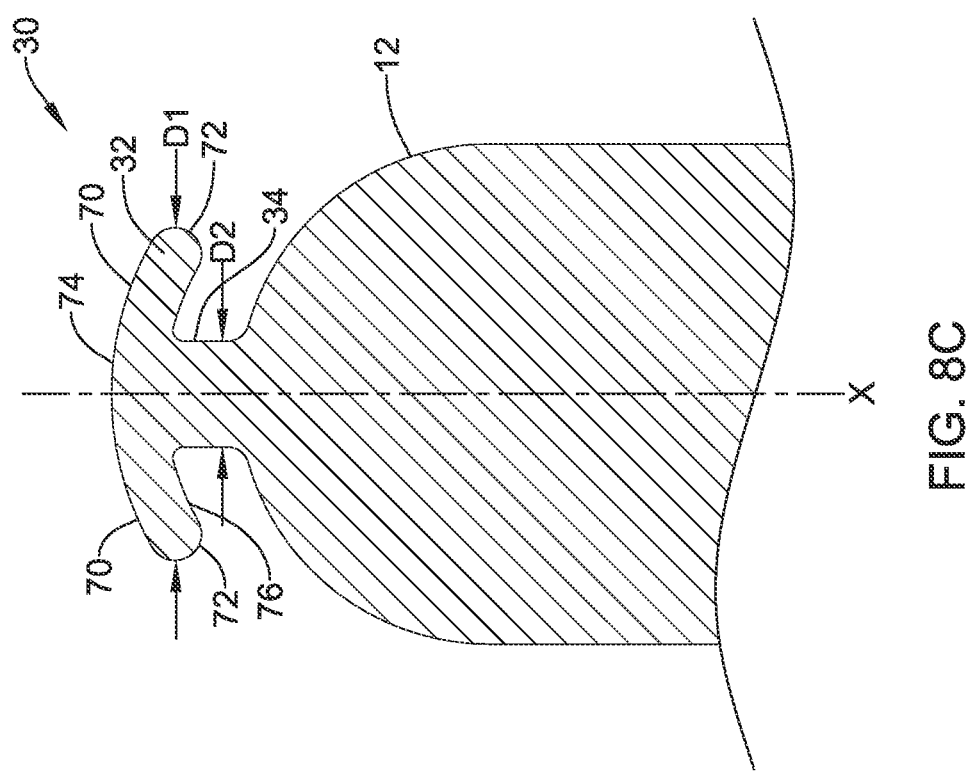

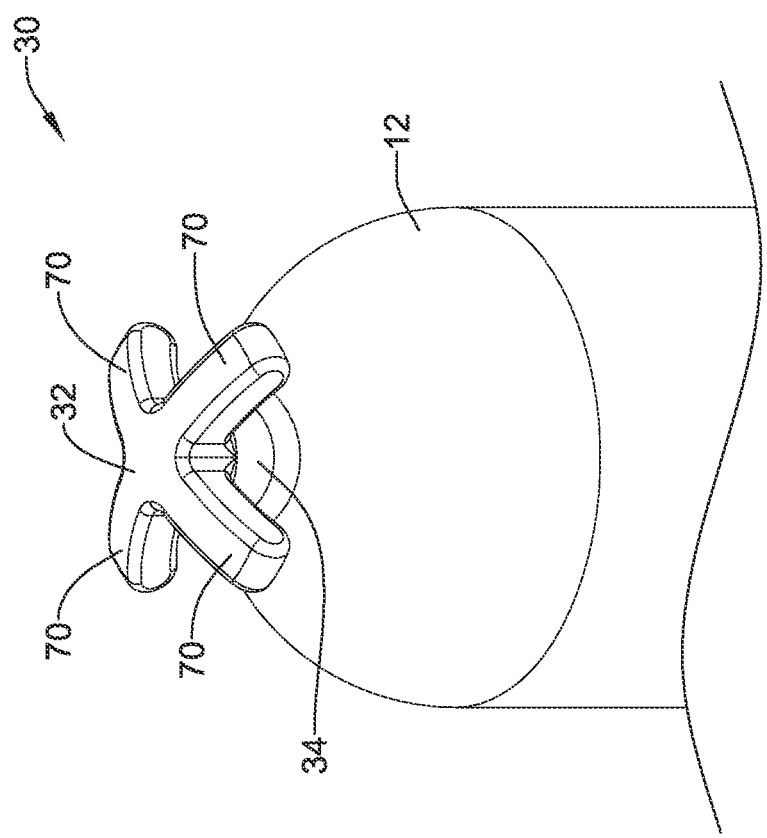

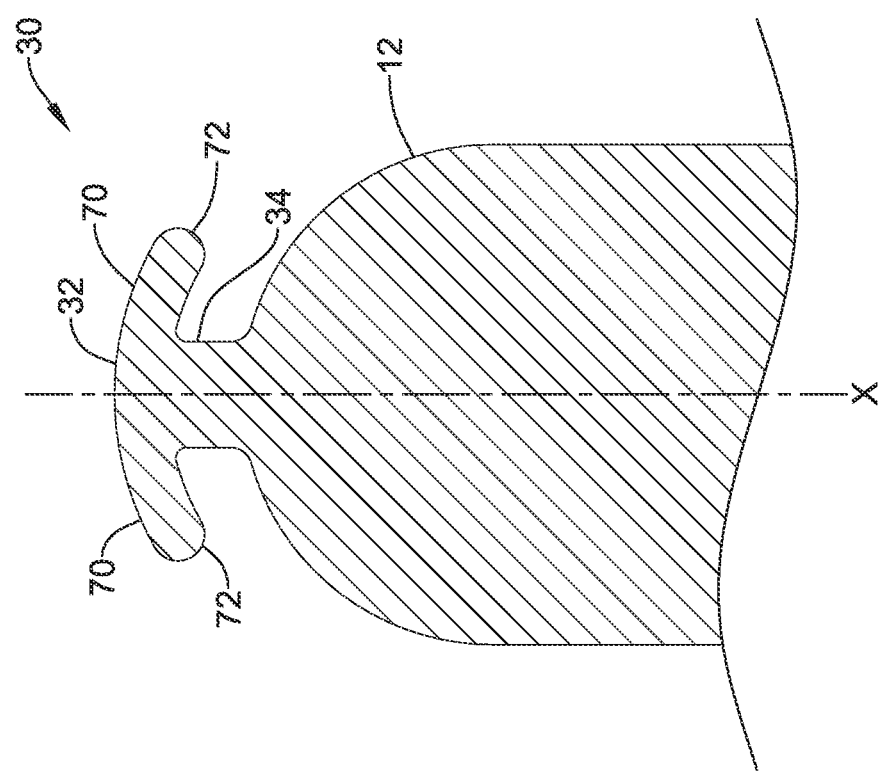

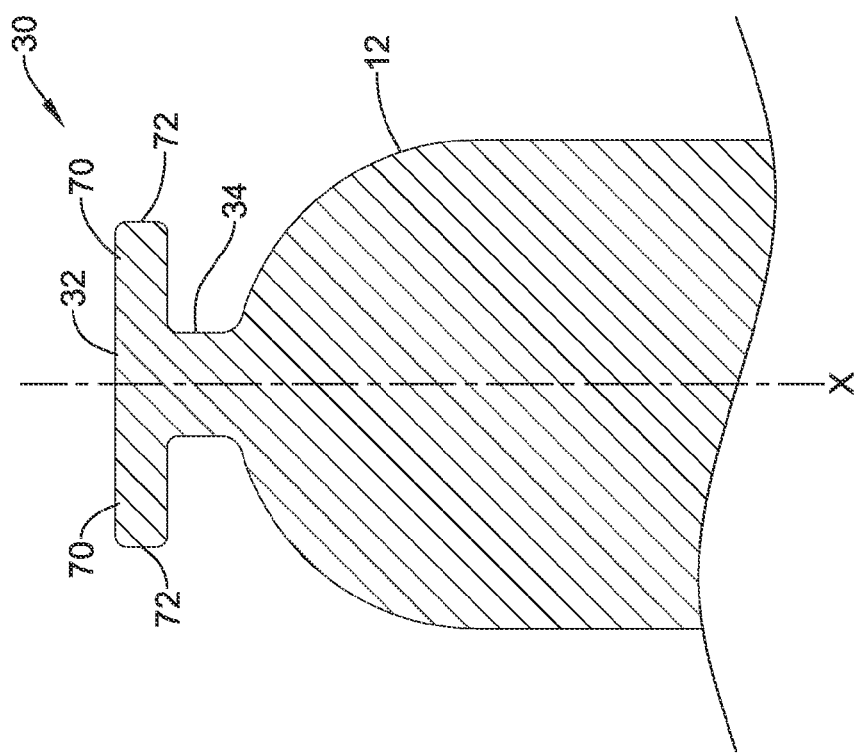

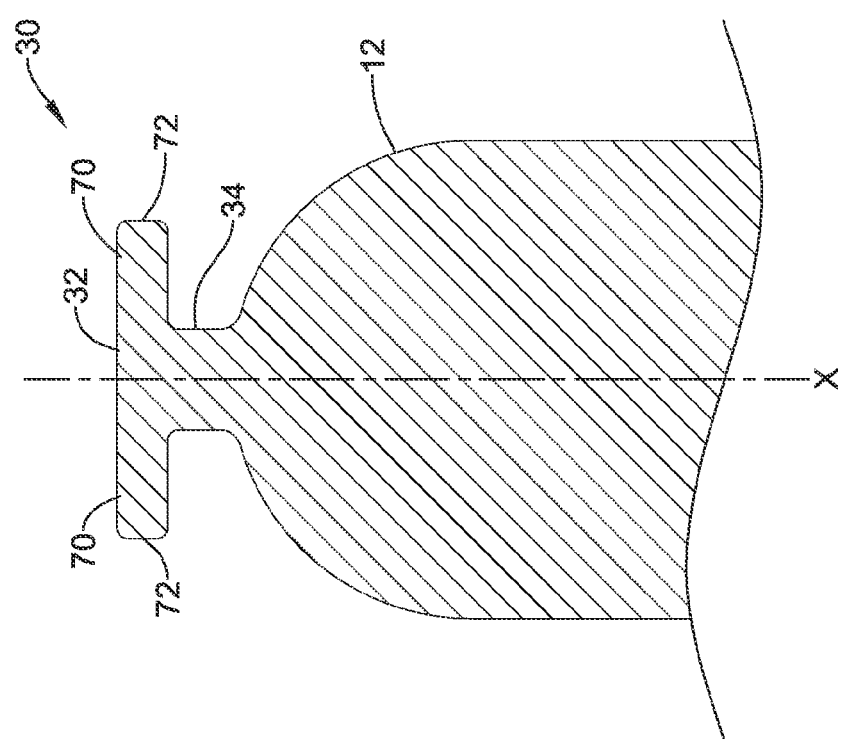

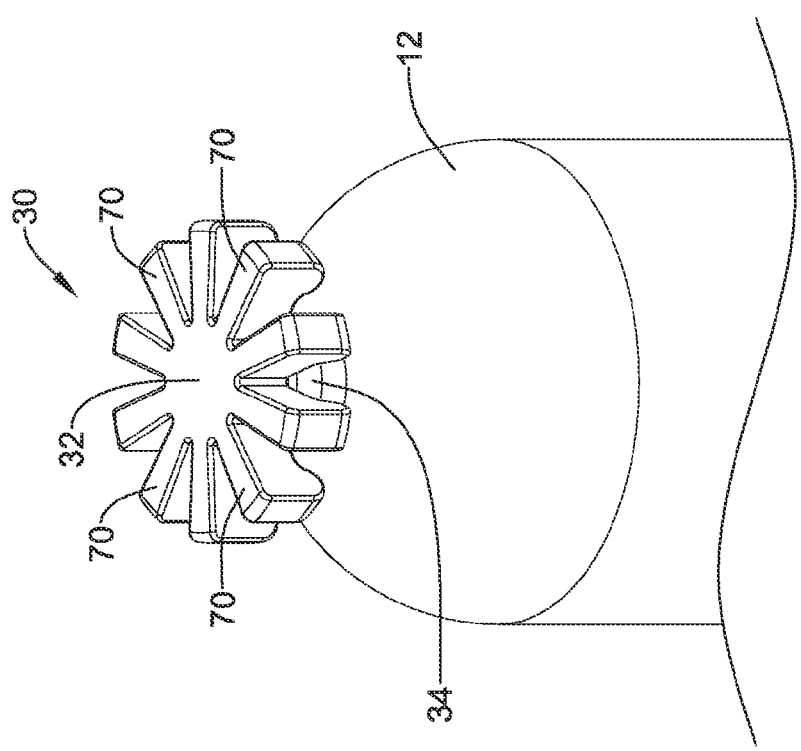

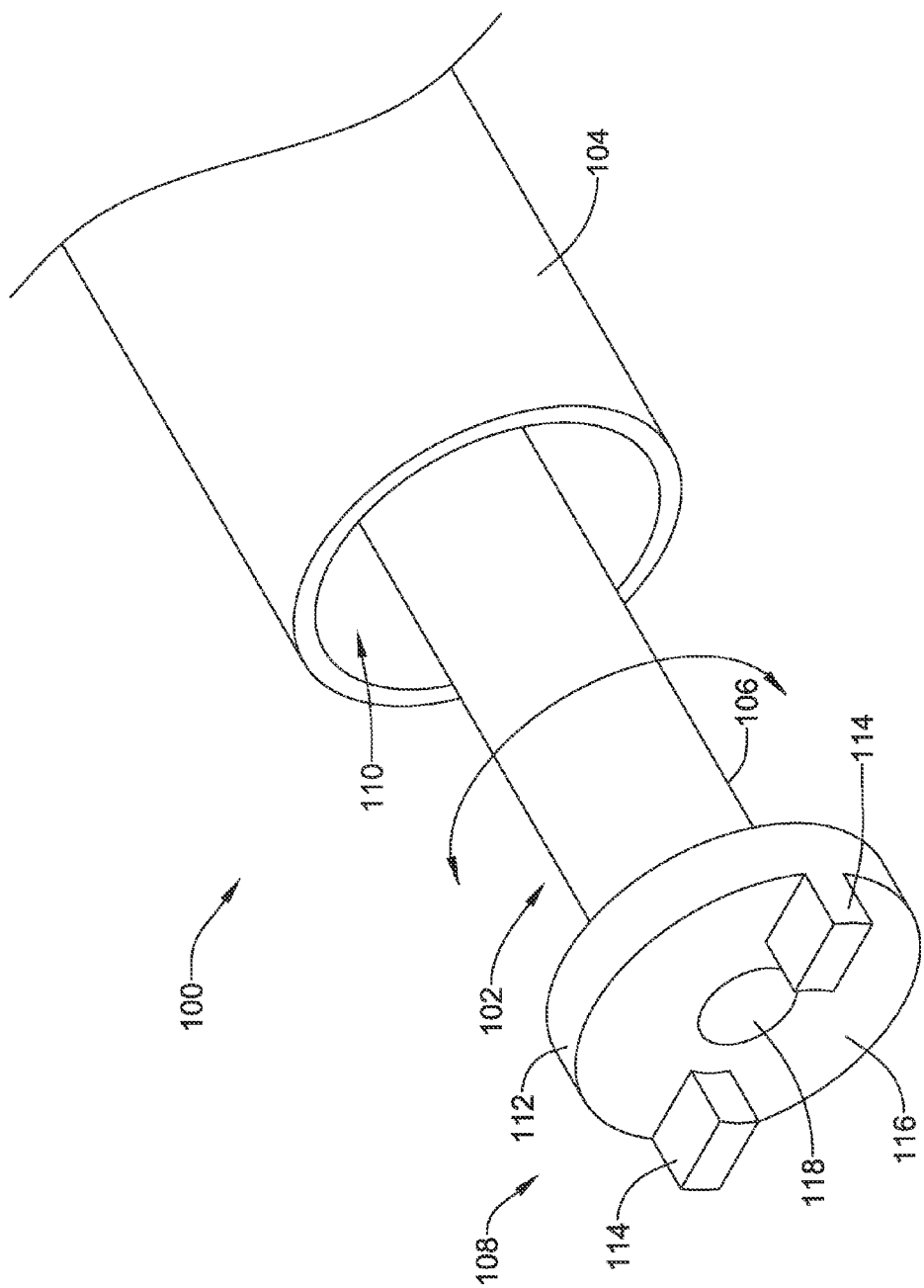

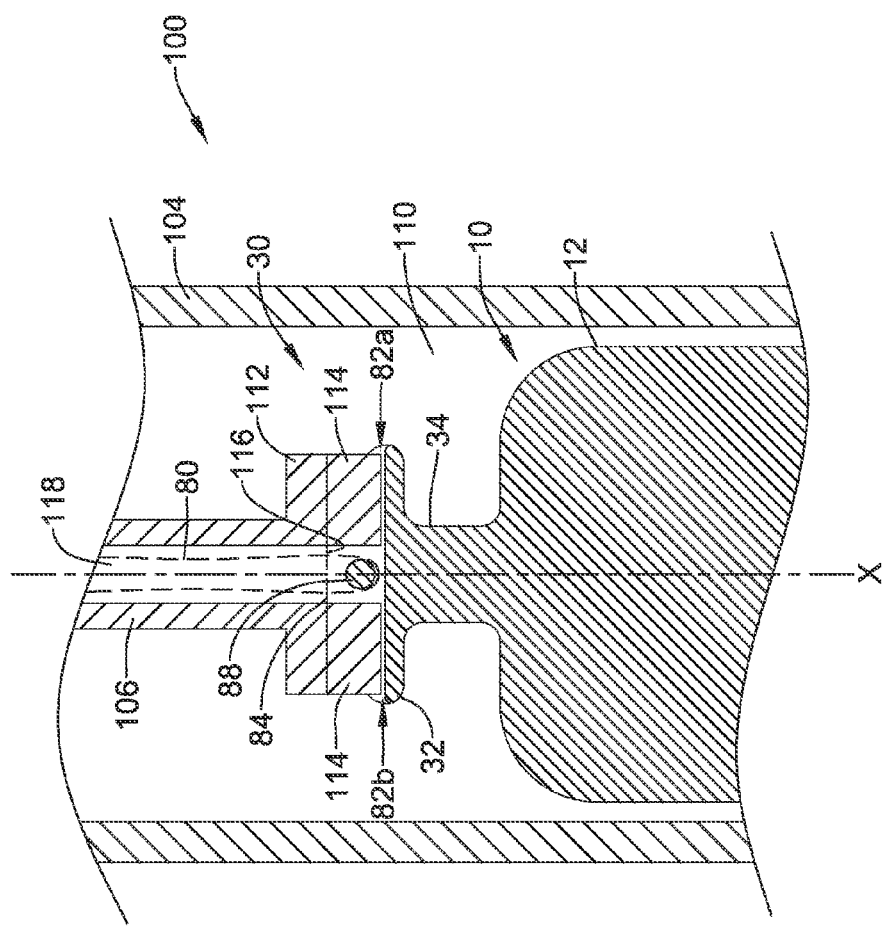

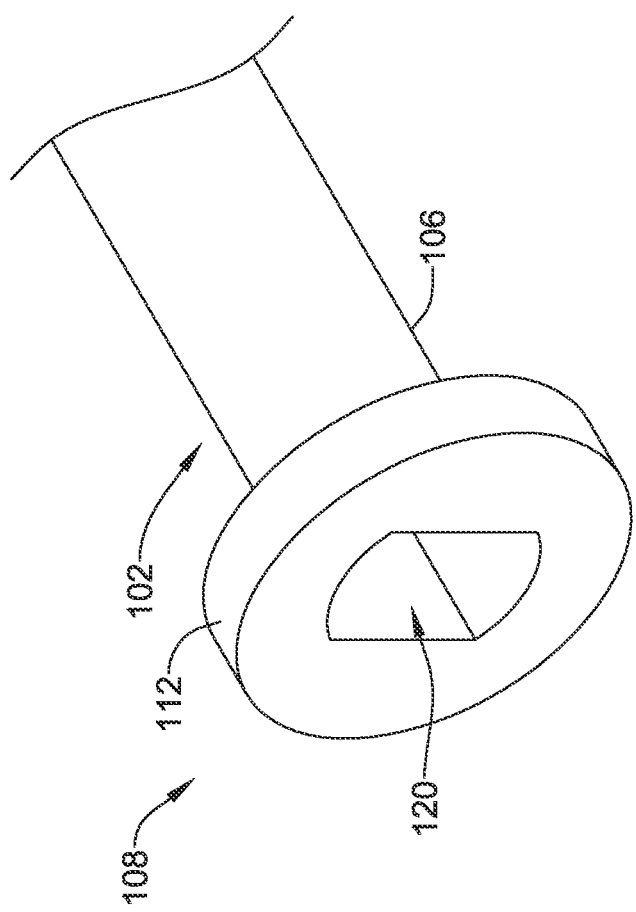

LEADLESS CARDIAC PACEMAKER WITH DELIVERY AND/OR RETRIEVAL FEATURES

CROSS-REFERENCES TO RELATED APPLICATIONS

This application claims the benefit of U.S. Provisional Application No. 61/866,644 filed Aug. 16, 2013, the complete disclosure of which is herein incorporated by reference.

TECHNICAL FIELD

The disclosure is directed to implantable cardiac devices. More particularly, the disclosure is directed to leadless cardiac stimulators or pacemakers including delivery and/or retrieval features.

BACKGROUND

Cardiac pacemakers provide electrical stimulation to heart tissue to cause the heart to contract and thus pump blood through the vascular system. Conventional pacemakers typically include an electrical lead that extends from a pulse generator implanted subcutaneously or sub-muscularly to an electrode positioned adjacent the inside or outside wall of the cardiac chamber. As an alternative to conventional pacemakers, self-contained or leadless cardiac pacemakers have been proposed. Leadless cardiac pacemakers are small capsules typically fixed to an intracardiac implant site in a cardiac chamber with a fixation mechanism engaging the intracardiac tissue. The small capsule typically includes bipolar pacing/sensing electrodes, a power source (e.g. a battery), and associated electrical circuitry for controlling the pacing/sensing electrodes, and thus provide electrical stimulation to heart tissue and/or sense a physiological condition.

Accordingly, there it is desirable to provide alternative structures to facilitate delivering leadless cardiac pacemakers to an implantation site in a heart chamber and/or retrieving leadless cardiac pacemakers from an implantation site in a heart chamber.

SUMMARY

The disclosure is directed to several alternative designs, materials and methods of manufacturing medical device structures and assemblies, and uses thereof.

Accordingly, one illustrative embodiment is an implantable leadless cardiac pacing device. The implantable device includes a housing, an electrode positioned proximate the distal end of the housing configured to be positioned adjacent cardiac tissue, and a docking member extending from the proximal end of the housing along a longitudinal axis of the housing. The docking member is configured to facilitate retrieval of the implantable leadless cardiac pacing device. The docking member includes a head portion and a neck portion extending between the housing and the head portion. The head portion has a radial dimension from the longitudinal axis and the neck portion has a radial dimension from the longitudinal axis less than the radial dimension of the head portion. The head portion includes a recess extending into the head portion from a proximal surface of the head portion for receiving a rotational driving instrument.

Another illustrative embodiment is an implantable leadless cardiac pacing device. The implantable device includes a housing, an electrode positioned proximate the distal end of the housing configured to be positioned adjacent cardiac tissue, and a docking member extending from the proximal end of the housing along a longitudinal axis of the housing. The docking member is configured to facilitate retrieval of the implantable leadless cardiac pacing device. The docking member includes a head portion and a neck portion extending between the housing and the head portion. The head portion has a radial dimension from the longitudinal axis and the neck portion has a radial dimension from the longitudinal axis less than the radial dimension of the head portion. The head portion includes a plurality of radially extending spokes extending radially outward from the longitudinal axis of the housing.

Another illustrative embodiment is a system for implanting an implantable leadless cardiac pacing device. The system includes an implantable cardiac pacing device and a delivery device. The implantable cardiac pacing device has a housing, an electrode positioned proximate a distal end of the housing, and a docking member extending from a proximal end of the housing opposite the distal end. The docking member includes a head portion and a neck portion extending between the housing and the head portion. The delivery device includes an elongate shaft and a driver mechanism at a distal end of the elongate shaft. The driver mechanism is configured for engagement with the head portion of the docking member. The driver mechanism includes a first lug configured to engage a recess extending into the head portion from a proximal surface of the head portion. In some instances, the driver mechanism includes first and second spaced apart lugs configured to engage first and second portions of the recess, respectively, with a member extending across the recess positioned between the first and second lugs.

Another illustrative embodiment is a system for retrieving an implantable leadless cardiac pacing device. The system includes an implantable cardiac pacing device and a retrieval device. The implantable cardiac pacing device has a housing having a longitudinal axis, an electrode positioned proximate a distal end of the housing, and a docking member extending from a proximal end of the housing opposite the distal end. The docking member includes a head portion and a neck portion extending between the housing and the head portion. The head portion includes a plurality of radially extending spokes extending radially outward from the longitudinal axis of the housing. The retrieval device includes a snare having an elongate shaft and one or more loops at a distal end of the elongate shaft. The one or more loops of the retrieval device are capable of encircling one or more of the radially extending spokes to capture the docking member with the snare.

Another illustrative embodiment is a method of implanting an implantable cardiac pacing device. The method includes advancing an implantable cardiac pacing device into a chamber of a heart with a delivery device. The implantable cardiac pacing device includes a helical fixation mechanism extending from a distal end of a housing of the implantable cardiac pacing device and a docking member extending from a proximal end of the housing. The docking member includes a head portion and a neck portion extending between the housing and the head portion. The method further includes rotating an elongate shaft of the delivery device to rotate the helical fixation mechanism into cardiac tissue. The delivery device includes a driver mechanism at a distal end of the elongate shaft. The driver mechanism includes a first lug engaged in a recess of the head portion of the docking member to transfer rotational motion from the driver mechanism to the implantable cardiac pacing device.

Yet another illustrative embodiment is a method of retrieving an implantable cardiac pacing device from a heart. The implantable cardiac pacing device has a housing having a longitudinal axis, an electrode positioned proximate a distal end of the housing, and a docking member extending from a proximal end of the housing opposite the distal end. The docking member includes a head portion and a neck portion extending between the housing and the head portion. The head portion includes a plurality of radially extending spokes extending radially outward from the longitudinal axis of the housing. The method includes advancing a snare into a heart having the implantable cardiac pacing device implanted therein and encircling the docking member with a loop of the snare. The loop is then cinched around a portion of the docking member and the snare is actuated proximally to pull the implantable cardiac pacing device into a lumen of a retrieval catheter.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIG. 3 illustrates another exemplary retrieval device capturing an implantable device during a retrieval procedure;

FIGS. 4A-4C illustrate an exemplary docking member of an implantable device;

FIGS. 7A-7C illustrate another exemplary docking member of an implantable device;

FIGS. 8A-8C illustrate another exemplary docking member of an implantable device;

FIGS. 9A-9C illustrate another exemplary docking member of an implantable device;

FIGS. 11A-11C illustrate another exemplary docking member of an implantable device;

FIGS. 12A-12C illustrate another exemplary docking member of an implantable device;

FIGS. 14A-14C illustrate another exemplary docking member of an implantable device;

FIG. 17A illustrates an exemplary delivery device for delivering an implantable device;

FIG. 17C illustrates the delivery device of FIG. 17A in engagement with the docking member of the implantable device of FIGS. 16A-16C; and FIGS. 18A-18D illustrate alternative embodiments of a driver mechanism for a rotational driving instrument.

Figure 1:
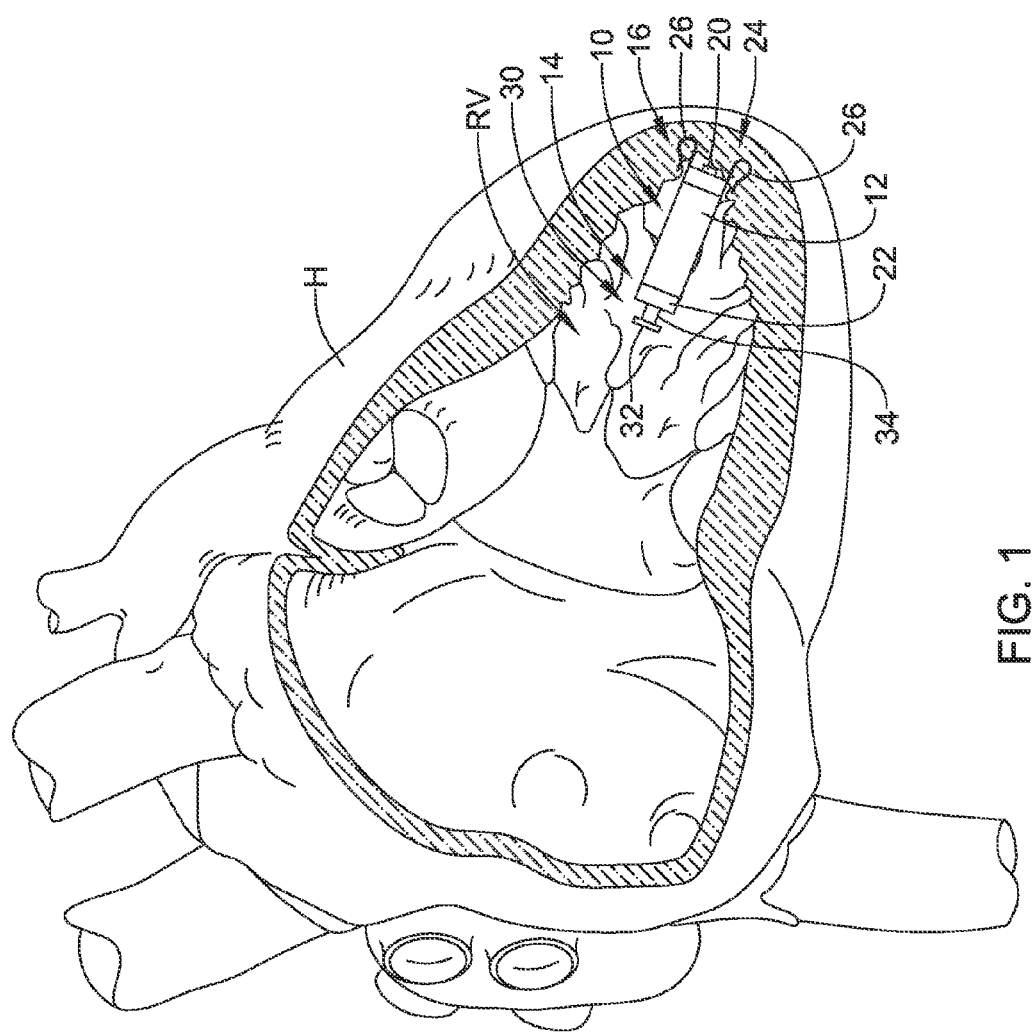
FIG. 1 illustrates an exemplary implantable device implanted in a chamber of a heart.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Referring to FIG. 1, an exemplary implantable leadless cardiac pacing device 10 (e.g., a leadless pacemaker) is illustrated implanted in a chamber of a heart H, such as the apex of the right ventricle RV. The implantable device 10 may include a shell or housing 12 having a proximal end 14 and a distal end 16. The implantable device 10 may include a first electrode 20 positioned proximate the distal end 16 of the housing 12 and a second electrode 22 positioned proximate the proximal end 14 of the housing 12. The electrodes 20, 22 may be sensing and/or pacing electrodes to provide electro-therapy and/or sensing capabilities. The first electrode 20 may be configured to be positioned against or otherwise contact the cardiac tissue of the heart H while the second electrode 22 may be spaced away from the first electrode 20, and thus spaced away from the cardiac tissue.

The implantable device 10 may include a pulse generator (e.g., electrical circuitry) and a power source (e.g., a battery) within the housing 12 to provide electrical signals to the electrodes 20, 22 and thus control the pacing/sensing electrodes 20, 22. Electrical communication between pulse generator and the electrodes 20, 22 may provide electrical stimulation to heart tissue and/or sense a physiological condition.

The implantable device 10 may include a fixation mechanism 24 proximate the distal end 16 of the housing 12 configured to attach the implantable device 10 to a tissue wall of the heart H, or otherwise anchor the implantable device 10 to the anatomy of the patient. As shown in FIG. 1, in some instances, the fixation mechanism 24 may include one or more, or a plurality of hooks 26 anchored into the cardiac tissue of the heart H to attach the implantable device 10 to a tissue wall. In other instances, the fixation mechanism 24 may include one or more, or a plurality of passive tines, configured to entangle with trabeculae within the chamber of the heart H and/or a helical fixation anchor configured to be screwed into a tissue wall to anchor the implantable device 10 to the heart H.

The implantable device 10 may include a docking member 30 proximate the proximal end 14 of the housing 12 configured to facilitate delivery and/or retrieval of the implantable device 10. For example, the docking member 30 may extend from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10. The docking member 30 may be configured to facilitate delivery of the implantable device 10 to the intracardiac site and/or retrieval of the implantable device 10 from the intracardiac site. Some exemplary embodiments of the docking member 30 are described in further detail herein.

Figure 2:
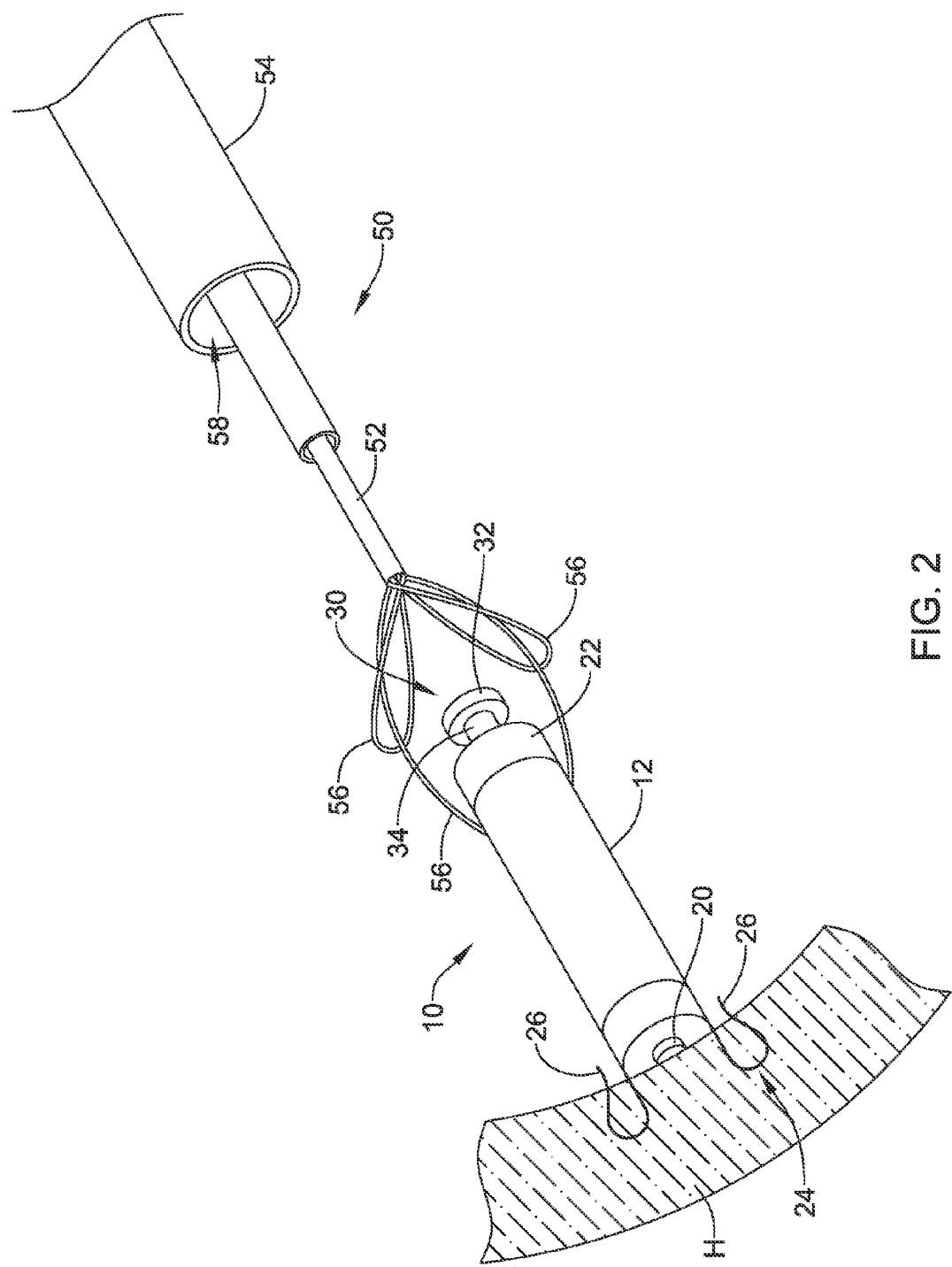
FIG. 2 illustrates an exemplary retrieval device capturing an implantable device during a retrieval procedure.

If it is desired to retrieve the implantable device 10 from the heart H, a retrieval device 50 may be advanced into the chamber of the heart H to capture the implantable device 10 and remove the implantable device 10 from the heart H. One exemplary retrieval device 50 is illustrated in FIG. 2. The retrieval device 50 may include a snare 52 advanceable from a lumen 58 of a retrieval catheter 54. The snare 52 may include one or more, or a plurality of loops 56 extending from a distal end of the snare 52 configured to engage the docking member 30 of the implantable device 10. The snare 52 shown in FIG. 2 includes three loops 56 formed by elongate filaments extending from the shaft of the snare 52. Once the loop(s) 56 of the snare 52 has captured the docking member 30, the snare 52 may be actuated proximally relative to the retrieval catheter 54 to pull the implantable device 10 into the lumen 58 of the retrieval catheter 54. The enlarged size of the head portion 32 relative to the neck portion 34 may permit the loop 56 of the snare 52 to encircle the neck portion 34 below (i.e., distal of) the head portion 32 and retain the loop 56 around the docking member 30 as the snare 52 is pulled proximally. As the implantable device 10 is pulled into the retrieval catheter 54, the fixation mechanism 24 may disengage from the heart tissue to detach the implantable device 10 from the heart wall. For example, the hooks 26 may elongate as the implantable device 10 is drawn proximally into the lumen 58 of the retrieval catheter 54. Thereafter, the retrieval device 50, with the implantable device 10 captured in the lumen of the retrieval catheter 54 with the snare 52, may be withdrawn from the heart H.

Another exemplary retrieval device 50 is illustrated in FIG. 3. Similar to FIG. 2, the retrieval device 50 may include a snare 52 advanceable from a lumen 58 of a retrieval catheter 54. The snare 52 may include one or more, or a plurality of loops 56 extending from a distal end of the snare 52 configured to engage the docking member 30 of the implantable device 10. The snare 52 shown in FIG. 3 includes a single loop 56 formed by an elongate filament extending from the shaft of the snare 52. Once the loop 56 of the snare 52 has captured the docking member 30, the snare 52 may be actuated proximally relative to the retrieval catheter 54 to pull the implantable device 10 into the lumen 58 of the retrieval catheter 54. The enlarged size of the head portion 32 relative to the neck portion 34 may permit the loop 56 of the snare 52 to encircle the neck portion 34 below (i.e., distal of) the head portion 32 and retain the loop 56 around the docking member 30 as the snare 52 is pulled proximally. As the implantable device 10 is pulled into the retrieval catheter 54, the fixation mechanism 30 may disengage from the heart tissue to detach the implantable device 10 from the heart wall. For example, the hooks 26 may elongate as the implantable device 10 is drawn proximally into the lumen 58 of the retrieval catheter 54. Thereafter, the retrieval device 50, with the implantable device 10 captured in the lumen of the retrieval catheter 54 with the snare 52, may be withdrawn from the heart H.

FIGS. 4A-4C illustrate one exemplary docking member 30 located at the proximal end 14 of the implantable device 10. The docking member 30 shown in FIGS. 4A-4C may include a head portion 32 and a neck portion 34 extending between the housing 12 and the head portion 32. The head portion 32 may be a generally spherically shaped ball, having a diameter D1 greater than the diameter D2 of the neck portion 34. The docking member 30 may also include a passage 36 extending through a portion of the docking member 30 to receive a tether 80 (shown in phantom lines) which will be further described later herein. For example, the passage 36 may extend through the head portion 32 from a first side to a second side of the head portion 32. The spherical shape of the head portion 32 may provide an atraumatic profile, inhibiting tissue growth or entanglement around the docking member 30.

Figure 5A:
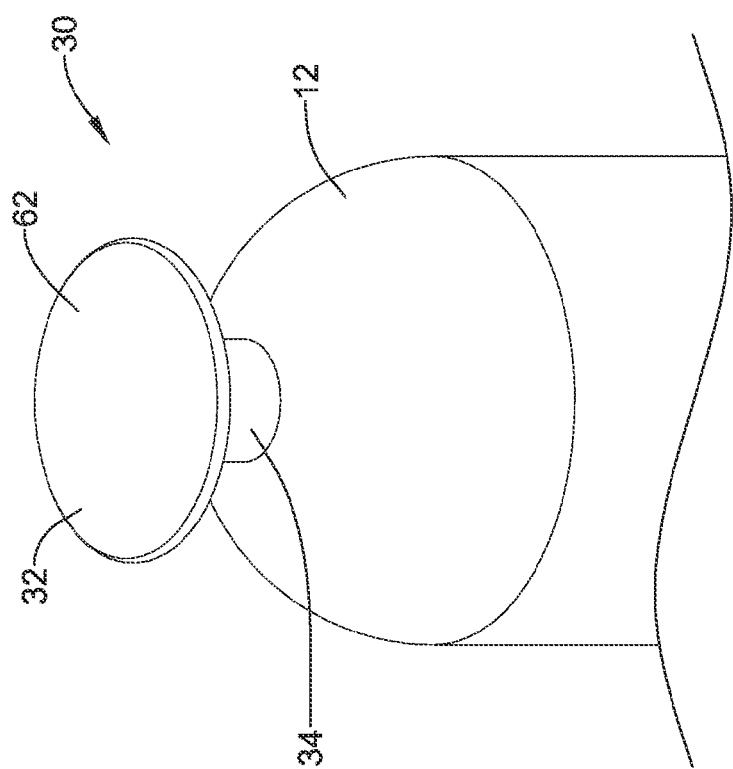
FIGS. 5A-5C illustrate another exemplary docking member of an implantable device.
Figure 5B:
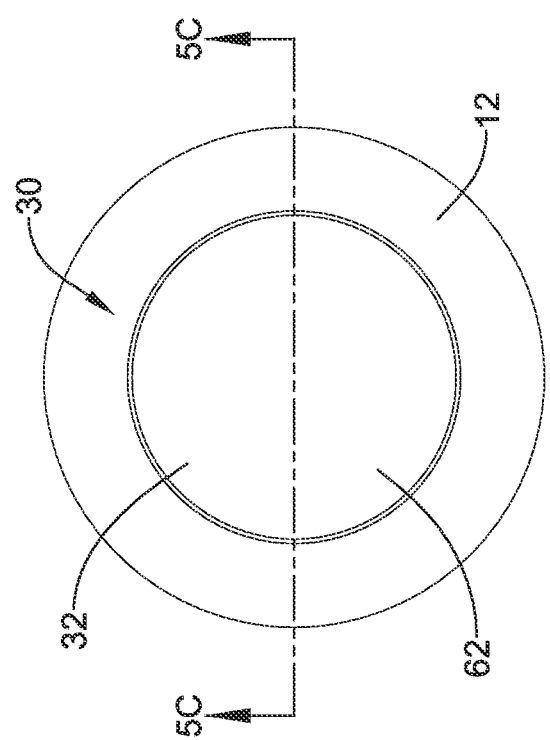
Figure 5C:
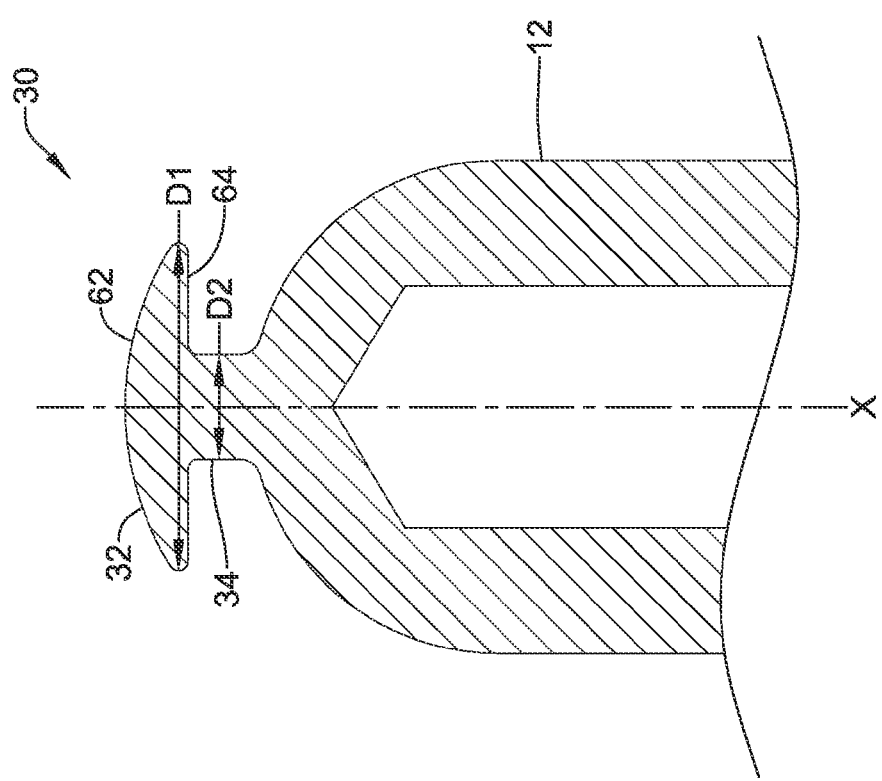

FIGS. 5A-5C illustrate another exemplary docking member 30 located at the proximal end 14 of the implantable device 10. The docking member 30 shown in FIGS. 5A-5C may include a head portion 32 and a neck portion 34 extending between the housing 12 and the head portion 32. The head portion 32 may be a generally disc shaped element having an upper surface 62 and an opposing lower surface 64. In some instances, the upper surface 62 and/or the lower surface 64 may be a spherically convex surface while in other instances the upper surface 62 and/or the lower surface 64 may be a spherically concave surface or a planar surface, for example. The head portion 32 may have a diameter D1 greater than the diameter D2 of the neck portion 34. Although not shown, the docking member 30 may also include a passage extending through a portion of the docking member 30 to receive a tether (described later herein). For example, a passage may extend through the head portion 32 from a first side to a second side of the head portion 32, or a passage may extend through the neck portion 34 from a first side to a second side of the neck portion 34. The shape of the head portion 32 may provide an atraumatic profile, inhibiting tissue growth or entanglement around the docking member 30.

Figure 6A:
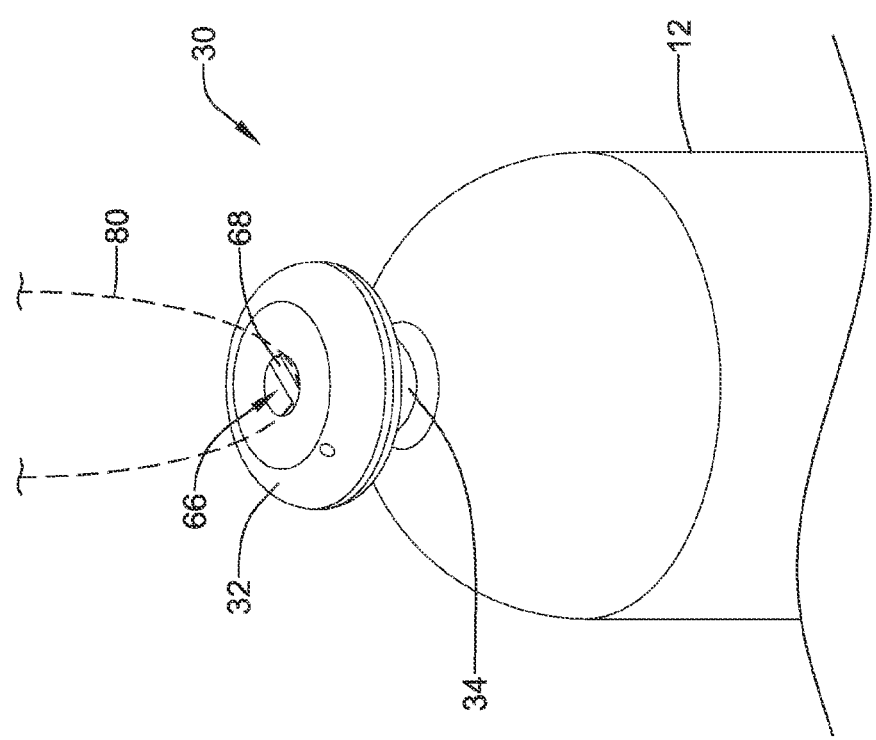
FIGS. 6A-6C illustrate another exemplary docking member of an implantable device.
Figure 6B:
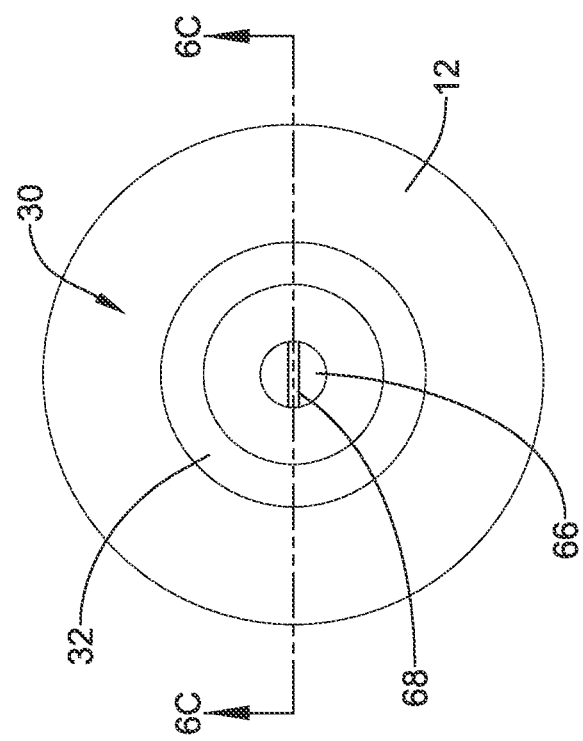
Figure 6C:
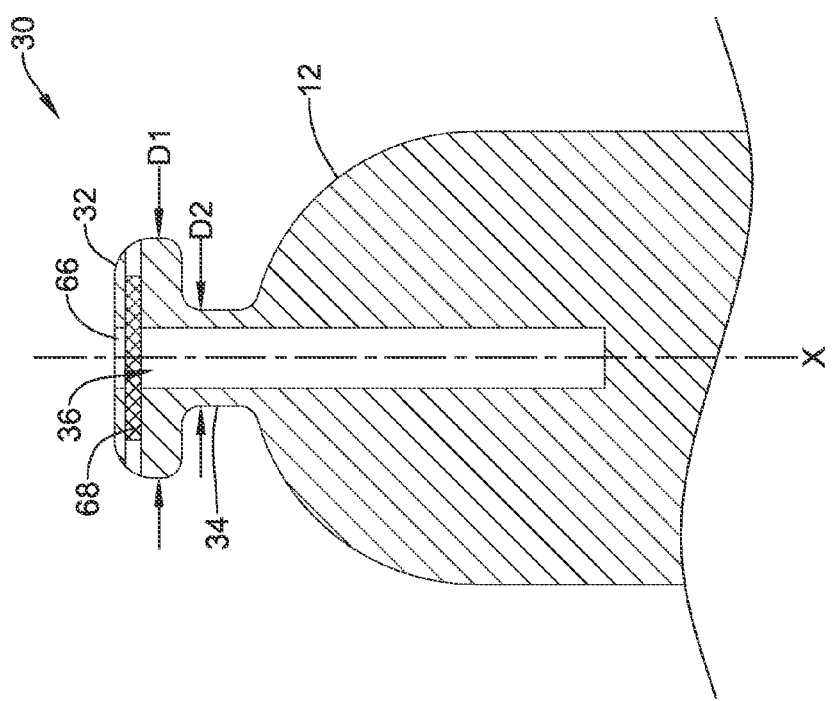

FIGS. 6A-6C illustrate another exemplary docking member 30 located at the proximal end 14 of the implantable device 10. The docking member 30 shown in FIGS. 6A-6C may include a head portion 32 and a neck portion 34 extending between the housing 12 and the head portion 32. The head portion 32 may be generally knob shaped, having a diameter D1 greater than the diameter D2 of the neck portion 34. The docking member 30 may also include a passage 36 extending through a portion of the docking member 30 to receive a tether 80 (shown in phantom) further described later herein. For example, the head portion 32 may include a central opening 66 extending into the head portion 32. A pin 68 may extend into or across the opening 66. For example, as shown in FIG. 6C the pin 68 may extend from a first side to a second side of the opening 66. In other instances, the pin 68 may extend into the opening 66 from a first side toward a second side of the opening 66, but not entirely across the opening 66 to the second side. The passage 36 may extend under the pin 68 such that the tether may be passed around the pin 68. The shape of the head portion 32 may provide an atraumatic profile, inhibiting tissue growth or entanglement around the docking member 30.

Figure 7B:
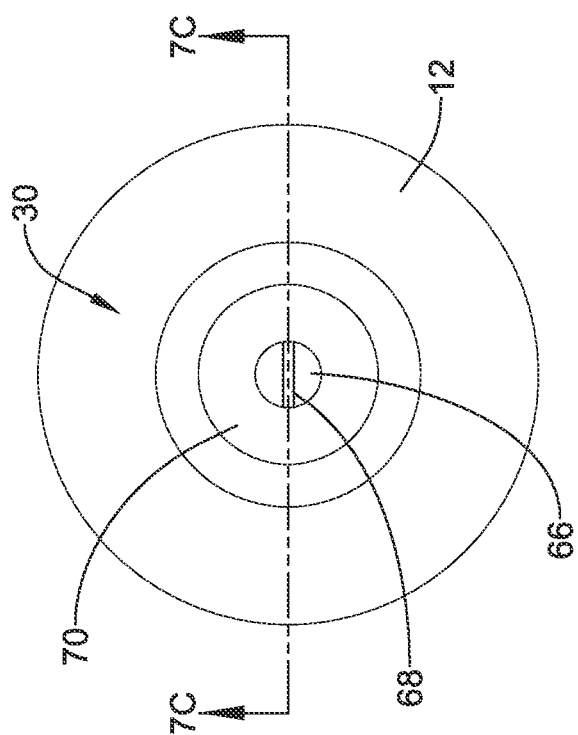
Figure 7C:
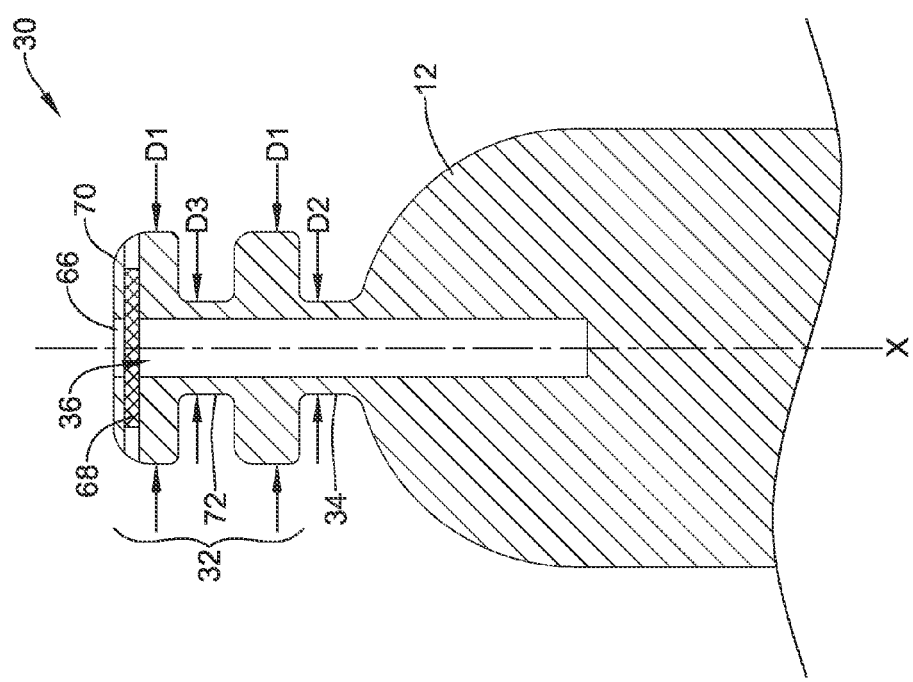

FIGS. 7A-7C illustrate another exemplary docking member 30 located at the proximal end 14 of the implantable device 10. The docking member 30 shown in FIGS. 7A-7C may include a head portion 32 and a neck portion 34 extending between the housing 12 and the head portion 32. The head portion 32 may include a plurality of enlarged portions 70 spaced apart by a reduced diameter necked portion 72. In some instances, the enlarged portions 70 may be generally knob shaped, having a diameter D1 greater than the diameter D3 of the necked portion between the enlarged portions 70 and the diameter D2 of the neck portion 34. Multiple enlarged portions 70 may facilitate engaging the docking member 30 with the loop(s) 56 of the snare 52 during retrieval of the implantable device 10. The shape of the head portion 32 may provide an atraumatic profile, inhibiting tissue growth or entanglement around the docking member 30.

The docking member 30 may also include a passage 36 extending through a portion of the docking member 30 to receive a tether (described later herein). For example, the head portion 32 may include a central opening 66 extending into the head portion 32. A pin 68 may extend into or across the opening 66. For example, as shown in FIG. 7C the pin 68 may extend from a first side to a second side of the opening 66. In other instances, the pin 68 may extend into the opening 66 from a first side toward a second side of the opening 66, but not entirely across the opening 66 to the second side. The passage 36 may extend under the pin 68 such that the tether may be passed around the pin 68.

Figure 8A:
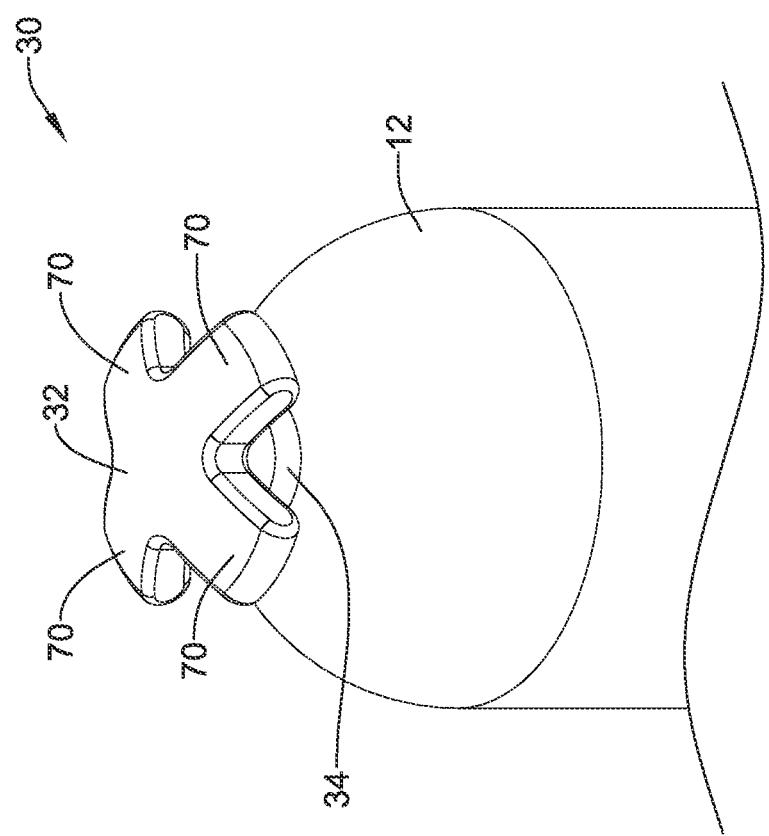
Figure 8B:
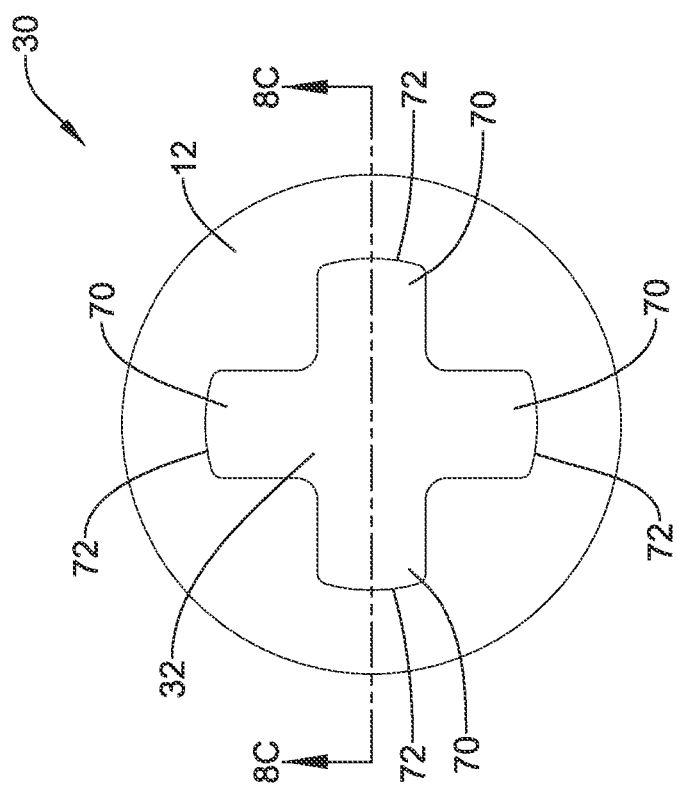

FIGS. 8A-8C illustrate another exemplary docking member 30 located at the proximal end 14 of the implantable device 10. The docking member 30 shown in FIGS. 8A-8C may include a head portion 32 and a neck portion 34 extending between the housing 12 and the head portion 32. The head portion 32 may have a diameter D1 greater than the diameter D2 of the neck portion 34. The head portion 32 may include a plurality of spokes 70 extending radially from the longitudinal axis of the implantable device 10, with spaces defined between adjacent spokes 70. The spokes 70 may be symmetrically or asymmetrically arranged around the longitudinal axis X. For example, the head portion 32 may include four spokes 70 uniformly arranged around the longitudinal axis X about 90 degrees apart. As shown in FIG. 8X, the free ends 72 of the radially extending spokes 70 may angle (e.g., curve) toward the distal end 16 of the implantable device 10, in some instances. For example, an upper surface 74 and/or a lower surface 76 of the spokes 70 may extend at an oblique angle to the longitudinal axis X of the implantable device 10 toward the distal end 16, such that the free ends 72 of the spokes 70 are positioned closer to the distal end 16 of the implantable device 10 than the base portion of the spokes 70 proximate the central longitudinal axis X. The configuration and/or arrangement of the spokes 70 may facilitate retention of the loop 56 of the snare 52 in engagement of the docking member 30 during retrieval of the implantable device 10. For example, the loop 56 may encircle one or more of the spokes 70 in addition to or instead of the neck portion 34.

Although not shown, the docking member 30 may also include a passage extending through a portion of the docking member 30 to receive a tether (described later herein). For example, a passage may extend through the one or more of the spokes 70 from a first side to a second side of the spoke 70, or a passage may extend through the neck portion 34 from a first side to a second side of the neck portion 34.

Figure 9B:
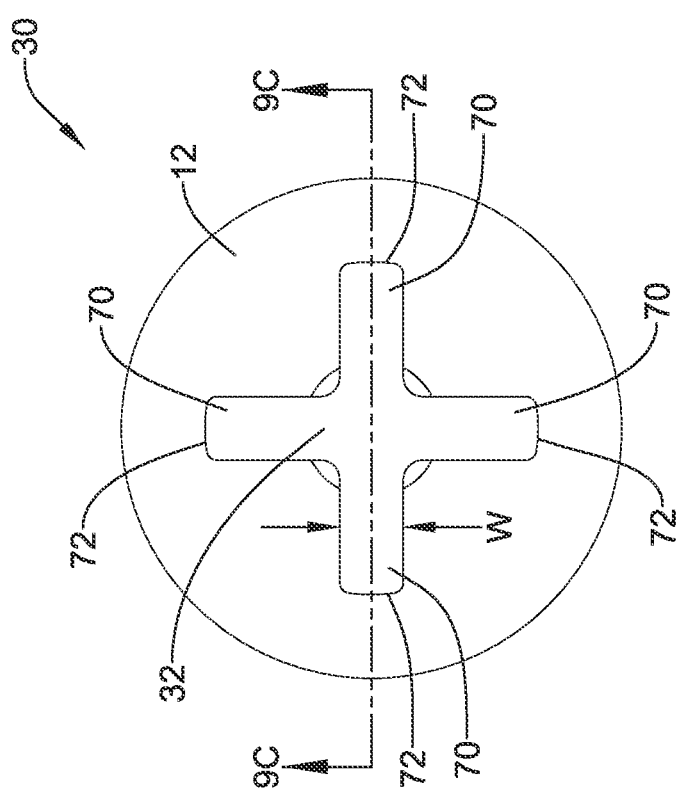

FIGS. 9A-9C illustrate another exemplary docking member 30 located at the proximal end 14 of the implantable device 10, similar to the docking member 30 illustrated in FIGS. 8A-8C. The docking member 30 shown in FIGS. 9A-9C may similarly include a plurality of spokes 70 extending radially from the longitudinal axis of the implantable device 10, with spaces defined between adjacent spokes 70, except the spokes 70 shown in FIGS. 9A-9C may have a width W less than the width of the spokes shown in FIGS. 8A-8C.

Although not shown, the docking member 30 may also include a passage extending through a portion of the docking member 30 to receive a tether (described later herein). For example, a passage may extend through the one or more of the spokes 70 from a first side to a second side of the spoke 70, or a passage may extend through the neck portion 34 from a first side to a second side of the neck portion 34.

Figure 10A:
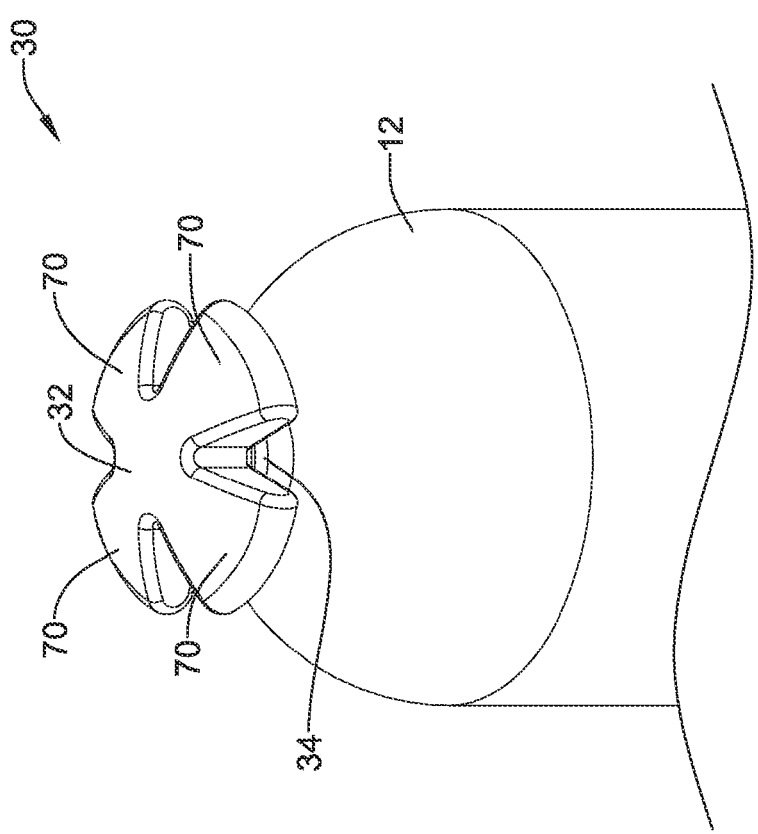
FIGS. 10A-10C illustrate another exemplary docking member of an implantable device.
Figure 10B:
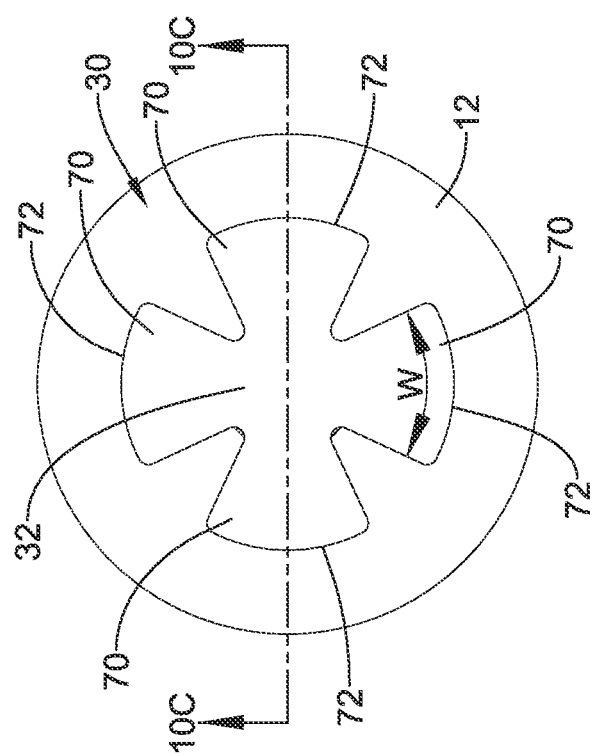
Figure 10C:
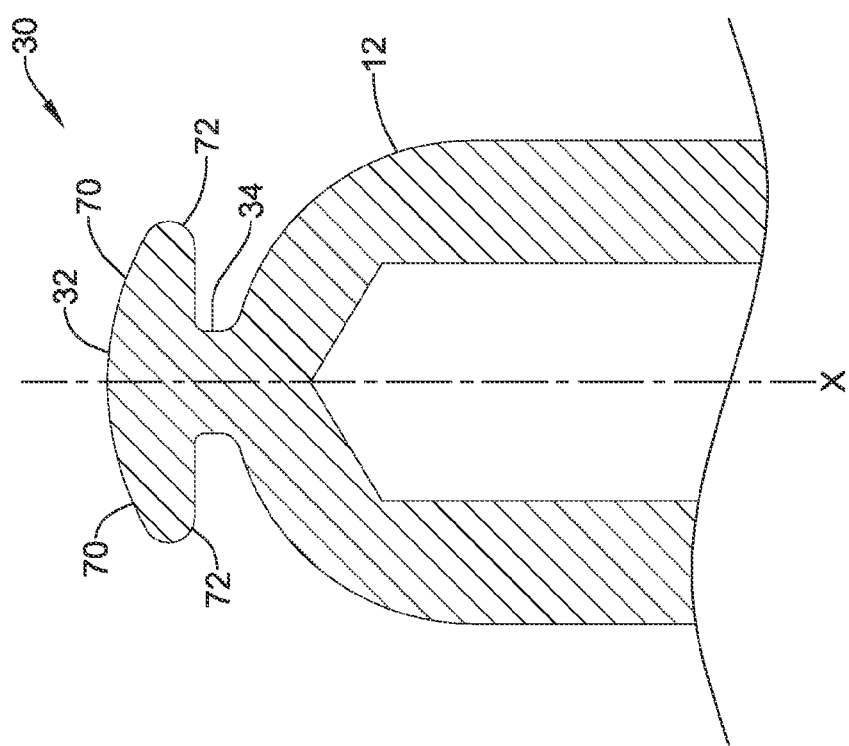

FIGS. 10A-10C illustrate another exemplary docking member 30 located at the proximal end 14 of the implantable device 10, similar to the docking member 30 illustrated in FIGS. 8A-8C. The docking member 30 shown in FIGS. 10A-10C may similarly include a plurality of spokes 70 extending radially from the longitudinal axis of the implantable device 10, with spaces defined between adjacent spokes 70. The width W of the spokes 70 shown in FIGS. 10A-10C may increase from the base portion toward the free ends 72 of the spokes. Thus, in instances in which the loop 56 of the snare 52 encircles one or more of the spokes 70, the enlarged free end 72 of the spokes 70 may prevent the loop 56 of the snare 52 from slipping off the spoke(s) 70 during retrieval of the implantable device 10.

Although not shown, the docking member 30 may also include a passage extending through a portion of the docking member 30 to receive a tether (described later herein). For example, a passage may extend through the one or more of the spokes 70 from a first side to a second side of the spoke 70, or a passage may extend through the neck portion 34 from a first side to a second side of the neck portion 34.

Figure 11A:
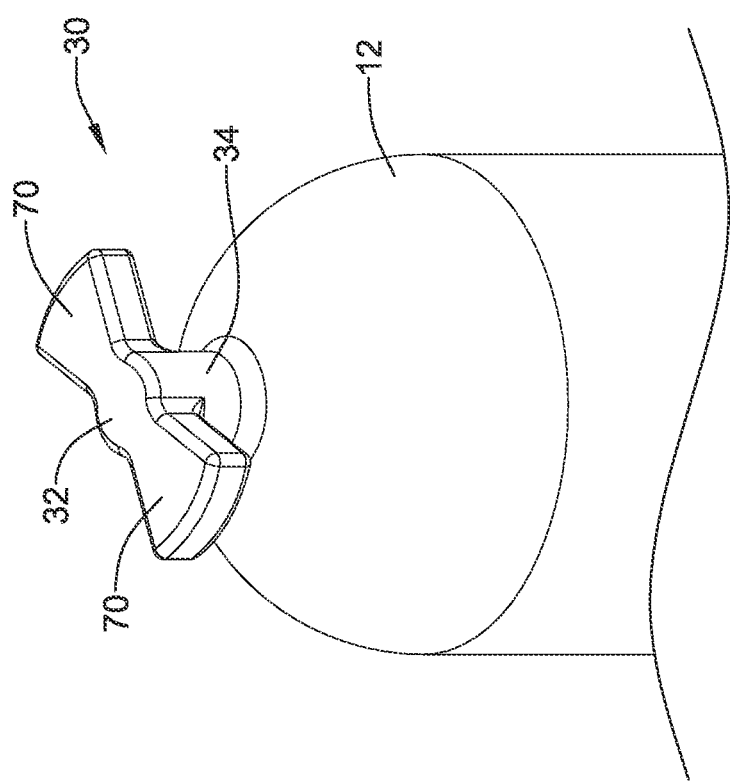
Figure 11B:
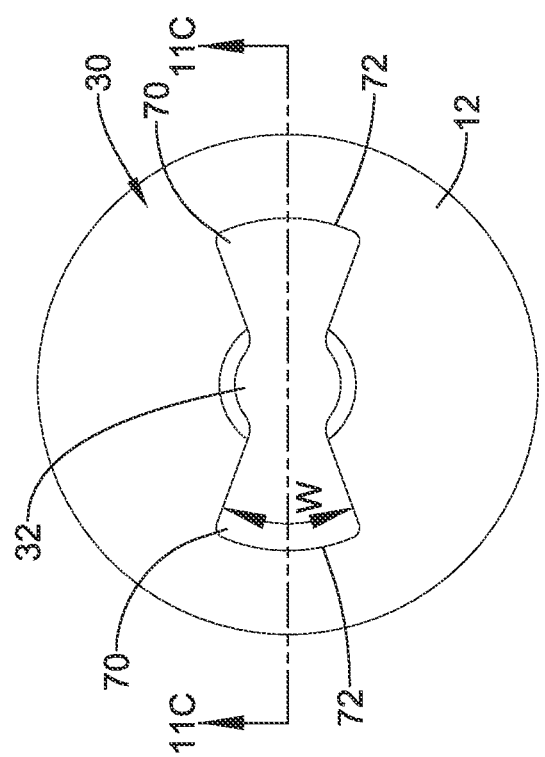

FIGS. 11A-11C illustrate another exemplary docking member 30 located at the proximal end 14 of the implantable device 10, similar to the docking member 30 illustrated in FIGS. 8A-8C. The docking member 30 shown in FIGS. 11A-11C may include a pair of spokes 70 extending radially from the longitudinal axis of the implantable device 10 in opposite directions. Similar to the spokes 70 shown in FIGS. 10A-10C, the width W of the spokes 70 shown in FIGS. 11A-11C may increase from the base portion toward the free ends 72 of the spokes. Thus, in instances in which the loop 56 of the snare 52 encircles one or more of the spokes 70, the enlarged free end 72 of the spokes 70 may prevent the loop 56 of the snare 52 from slipping off the spoke(s) 70 during retrieval of the implantable device 10.

Although not shown, the docking member 30 may also include a passage extending through a portion of the docking member 30 to receive a tether (described later herein). For example, a passage may extend through the one or more of the spokes 70 from a first side to a second side of the spoke 70, or a passage may extend through the neck portion 34 from a first side to a second side of the neck portion 34.

Figure 12A:
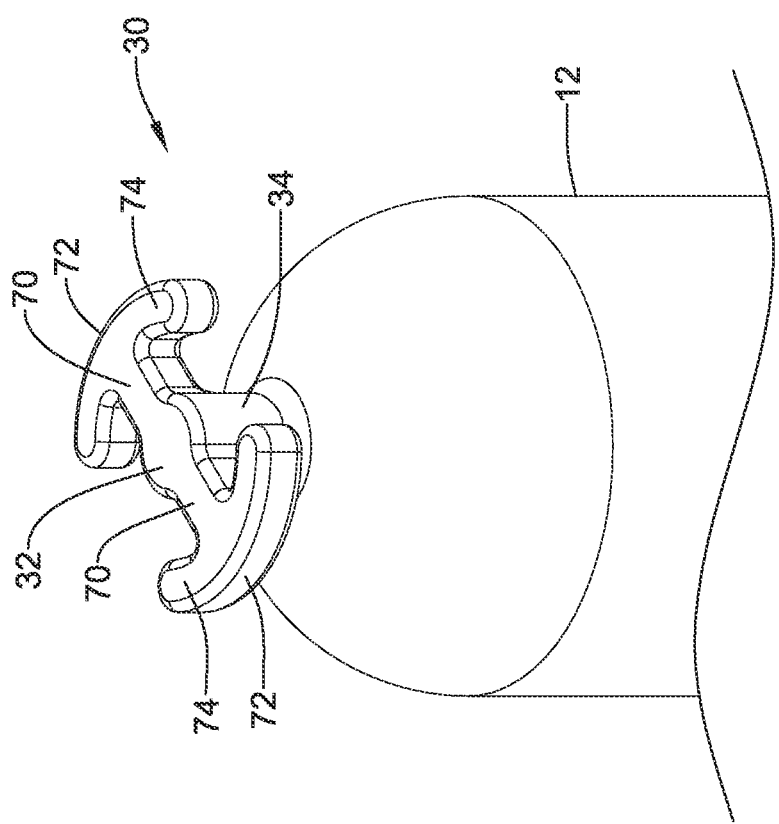
Figure 12B:
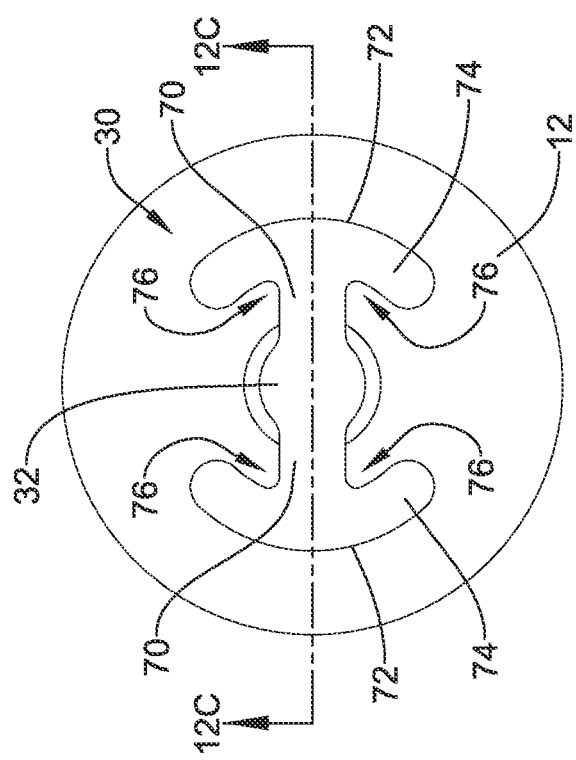

FIGS. 12A-12C illustrate another exemplary docking member 30 located at the proximal end 14 of the implantable device 10, similar to the docking member 30 illustrated in FIGS. 11A-11C. The docking member 30 shown in FIGS. 12A-12C may include a pair of spokes 70 extending radially from the longitudinal axis of the implantable device 10 in opposite directions. The free ends 72 of the spokes 70 may include a crossing member 74 extending transverse to the radial direction of the spokes 70. In some instances, the crossing member 74 may extend in opposite directions from the body of the spoke 70, or the crossing member 74 may extend in one transverse direction from the body of the spoke 70. For example, in some instances, the spokes 70 may have a T shape, a mushroom shape, an L shape, a V shape, or other desired shape. In some instances, the crossing member 74 may form an undercut 76 with the body of the spoke 70. The loop 56 of the snare 52 may be engaged in the undercuts 76 as the loop 56 is tightened around the spoke 70. In instances in which the loop 56 of the snare 52 encircles one or more of the spokes 70, the crossing member 74 at the free end 72 of the spokes 70 may prevent the loop 56 of the snare 52 from slipping off the spoke(s) 70 during retrieval of the implantable device 10.

Although not shown, the docking member 30 may also include a passage extending through a portion of the docking member 30 to receive a tether (described later herein). For example, a passage may extend through the one or more of the spokes 70 from a first side to a second side of the spoke 70, or a passage may extend through the neck portion 34 from a first side to a second side of the neck portion 34.

Figure 13A:
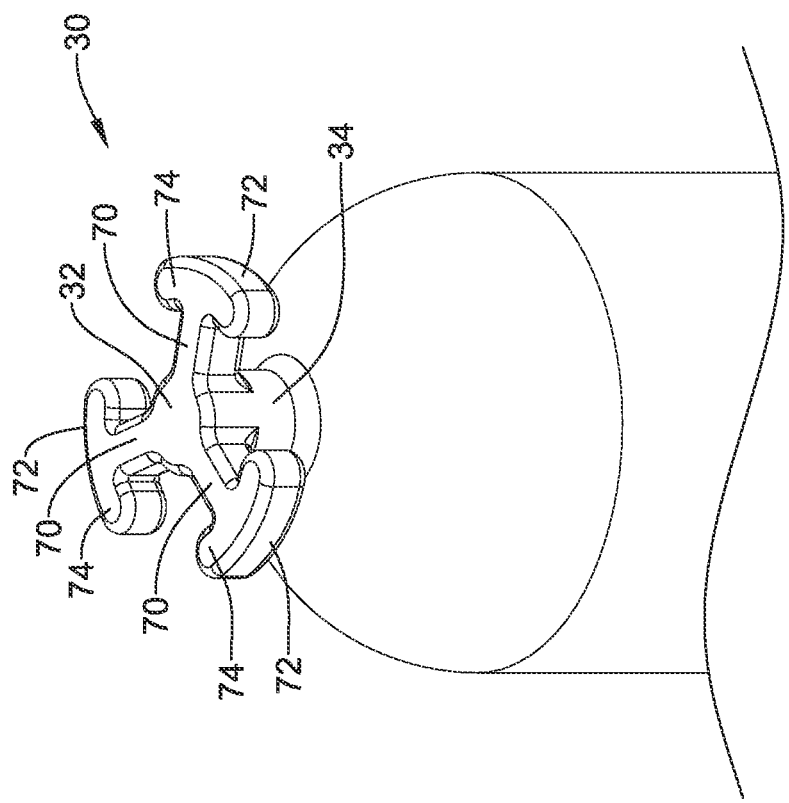
FIGS. 13A-13C illustrate another exemplary docking member of an implantable device.
Figure 13B:
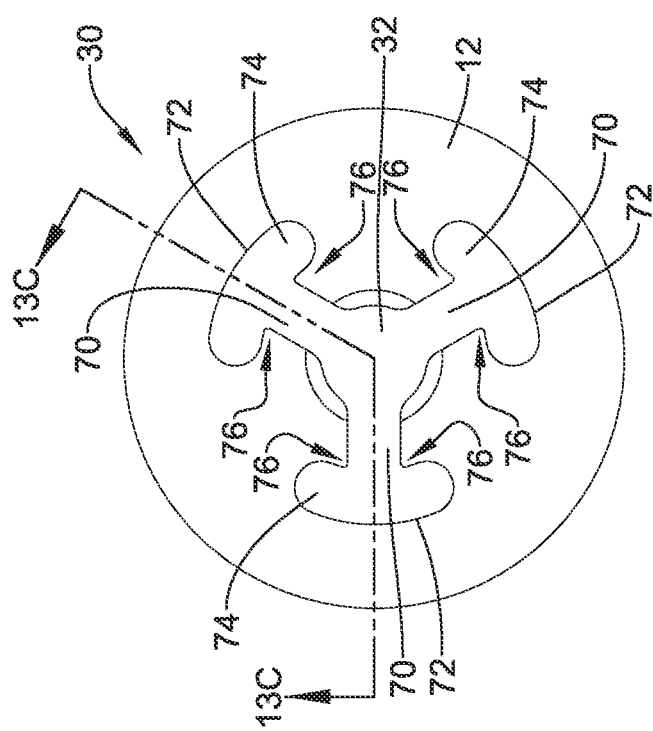
Figure 13C:
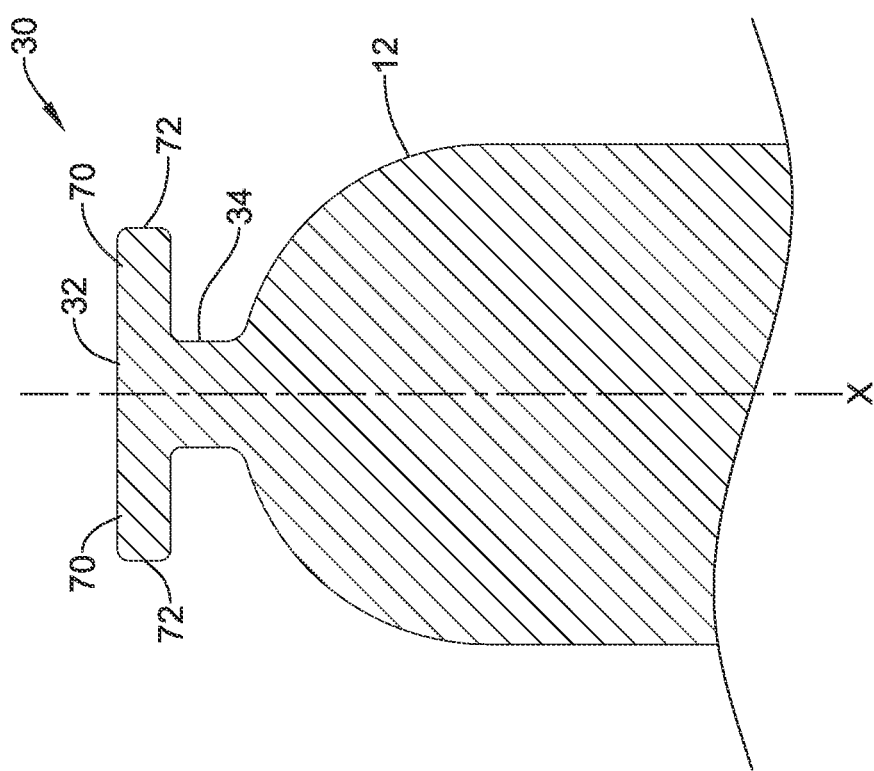

FIGS. 13A-13C illustrate another exemplary docking member 30 located at the proximal end 14 of the implantable device 10, similar to the docking member 30 illustrated in FIGS. 12A-12C. The docking member 30 shown in FIGS. 13A-13C may include a plurality of spokes 70 extending radially from the longitudinal axis of the implantable device 10, with spaces defined between adjacent spokes 70. The spokes 70 may be symmetrically or asymmetrically arranged around the longitudinal axis. For example, the head portion 32 may include three spokes 70 uniformly arranged around the longitudinal axis about 120 degrees apart. Similar to the spokes illustrated in FIGS. 12A-12C, the free ends 72 of the spokes 70 may include a crossing member 74 extending transverse to the radial direction of the spokes 70. In some instances, the crossing member 74 may extend in opposite directions from the body of the spoke 70, or the crossing member 74 may extend in one transverse direction from the body of the spoke 70. For example, in some instances, the spokes 70 may have a T shape, a mushroom shape, an L shape, a V shape, or other desired shape. In some instances, the crossing member 74 may form an undercut 76 with the body of the spoke 70. The loop 56 of the snare 52 may be engaged in the undercuts 76 as the loop 56 is tightened around the spoke 70. In instances in which the loop 56 of the snare 52 encircles one or more of the spokes 70, the crossing member 74 at the free end 72 of the spokes 70 may prevent the loop 56 of the snare 52 from slipping off the spoke(s) 70 during retrieval of the implantable device 10.

Although not shown, the docking member 30 may also include a passage extending through a portion of the docking member 30 to receive a tether (described later herein). For example, a passage may extend through the one or more of the spokes 70 from a first side to a second side of the spoke 70, or a passage may extend through the neck portion 34 from a first side to a second side of the neck portion 34.

Figure 14B:
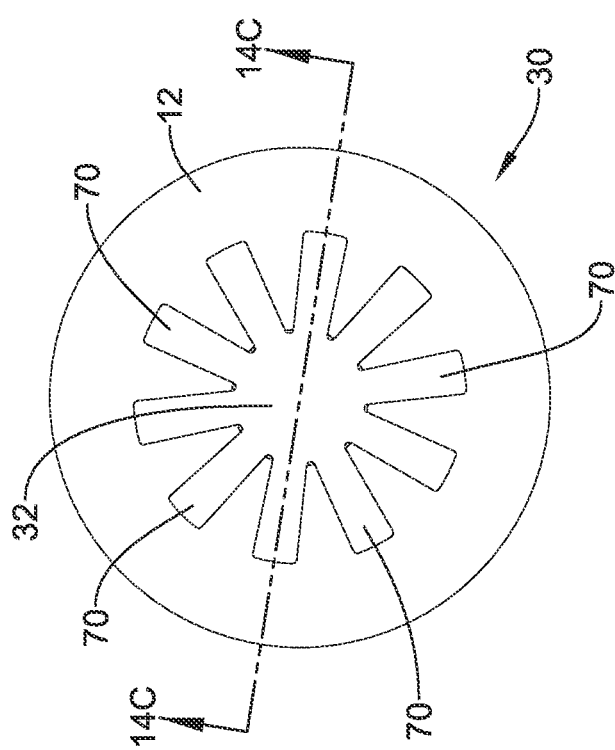
Figure 14C:
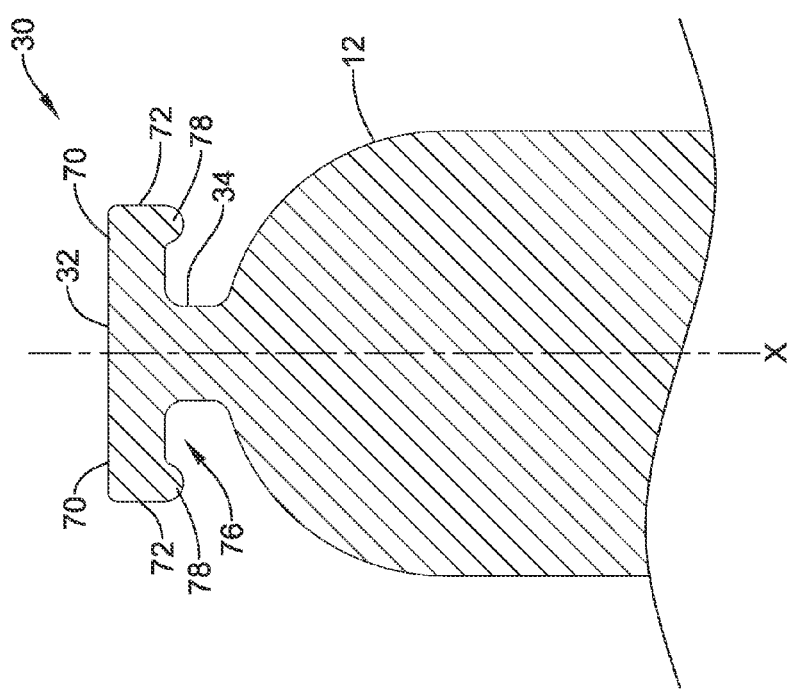

FIGS. 14A-14C illustrate another exemplary docking member 30 located at the proximal end 14 of the implantable device 10, similar to the docking member 30 illustrated in FIGS. 8A-8C. The docking member 30 shown in FIGS. 14A-14C may similarly include a plurality of spokes 70 extending radially from the longitudinal axis of the implantable device 10, with spaces defined between adjacent spokes 70. The docking member 30 may include any number of radially extending spokes 70 symmetrically or asymmetrically arranged around the longitudinal axis of the implantable device 10. For example, the docking member 30 may include 3, 4, 5, 6, 7, 8, 9, 10, 11, 12 or more radially extending spokes 70 in some instances.

As shown in FIG. 14C, the free ends 72 of the spokes 70 may include a distally projecting lip 78 relative to the body portion of the spokes 70. The distally projecting lips 78 may prevent the loop 56 of the snare 52 from slipping off the spoke(s) 70 during retrieval of the implantable device 10.

The configuration and/or arrangement of the spokes 70 may facilitate retention of the loop 56 of the snare 52 in engagement of the docking member 30 during retrieval of the implantable device 10. For example, the loop 56 may encircle one or more of the spokes 70 in addition to or instead of the neck portion 34.

In some instances it may be desirable to apply rotational motion to the implantable device 10 during delivery and/or retrieval of the implantable device 10. For example, in some embodiments such as the embodiment shown in FIG. 15A, the implantable device 10 may include a helical fixation anchor 90 at the distal end 16 of the housing 12 configured to be screwed into a tissue wall through rotational motion of the implantable device 10 to anchor the implantable device 10 to the heart H. In such instances, the docking member 30 may include an engagement feature configured to mate with an engagement feature of a delivery device to transfer rotational motion from a rotatable shaft of the delivery device to the implantable device 10.

Figure 15A:
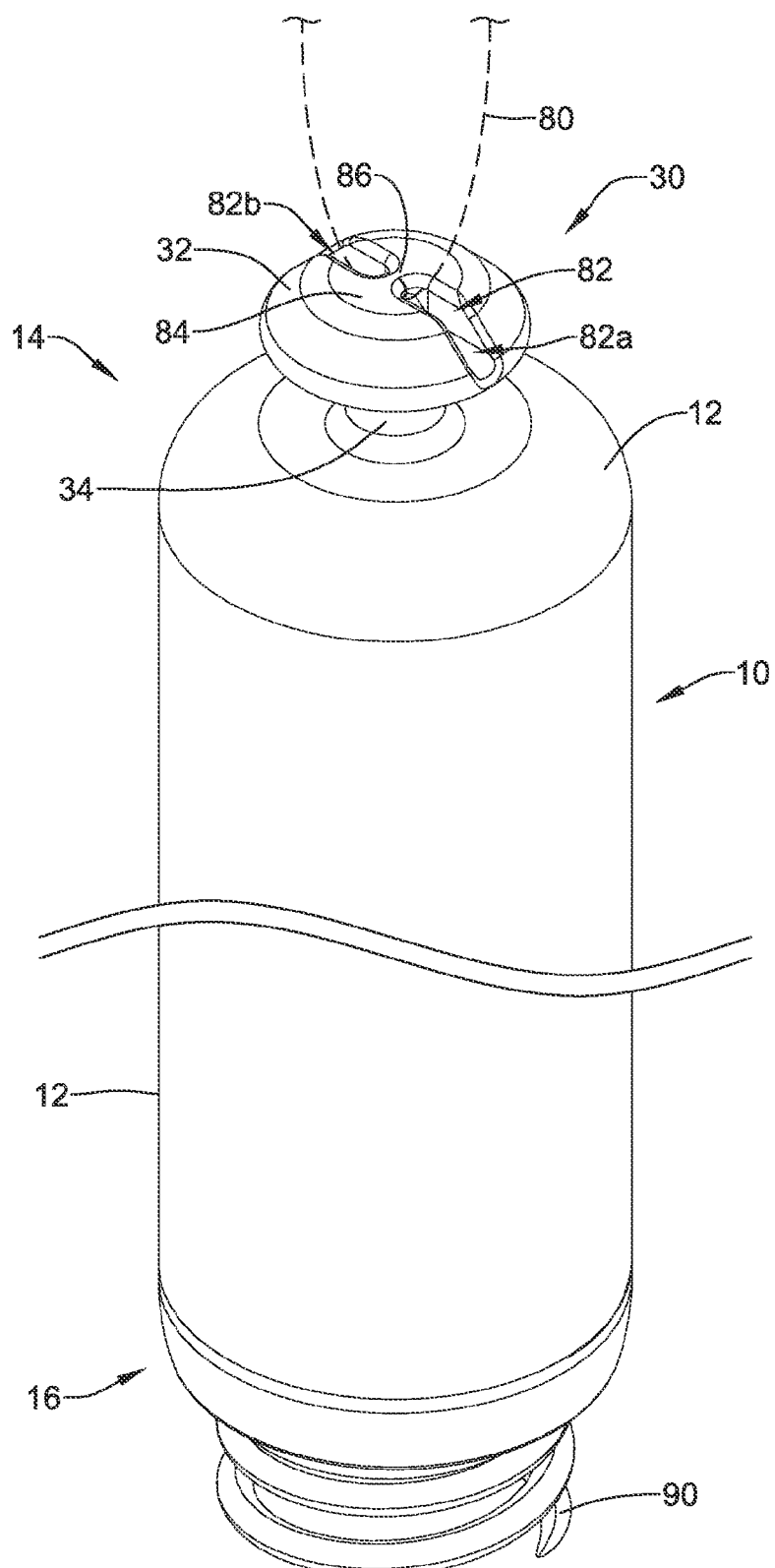
FIGS. 15A-15C illustrate another exemplary docking member of an implantable device.
Figure 15B:
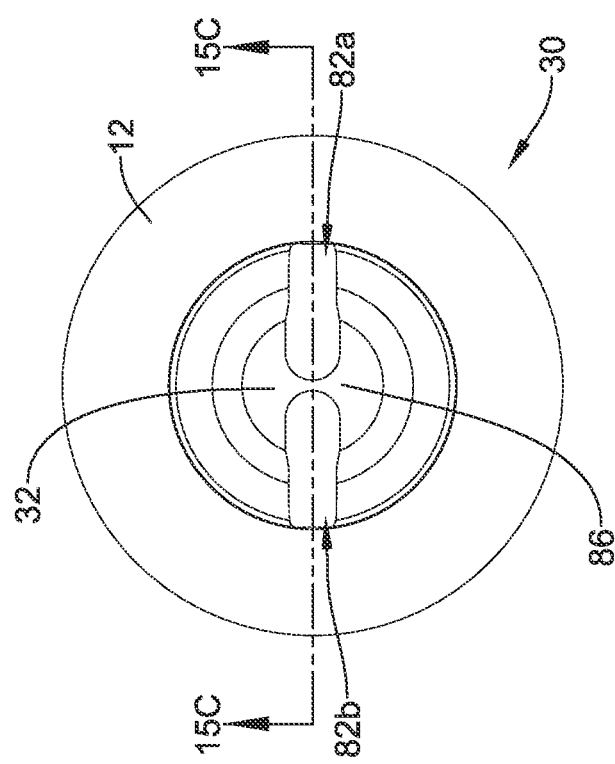
Figure 15C:
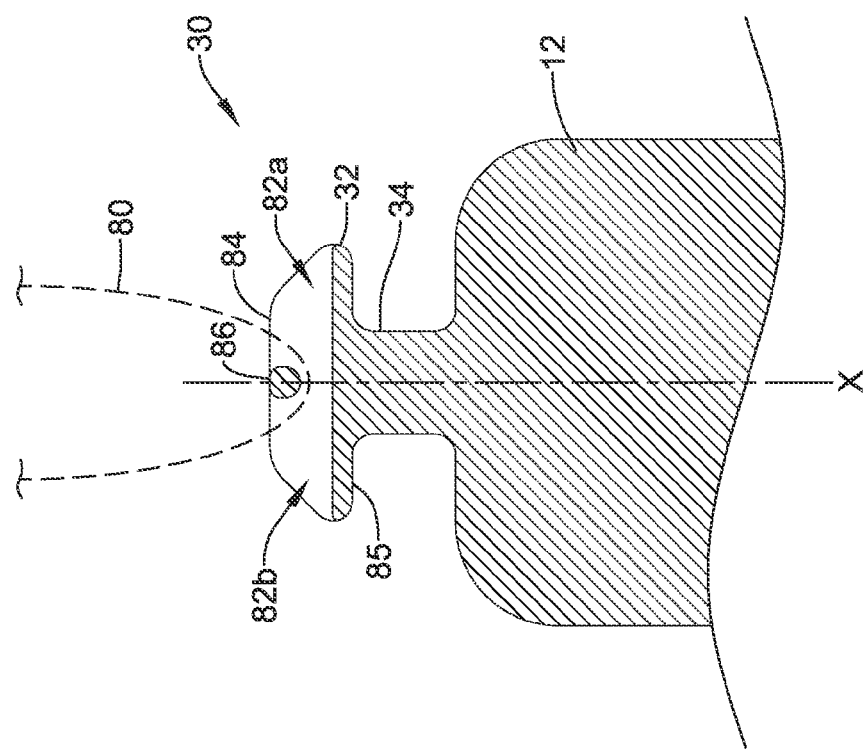

For example, in the embodiment of FIGS. 15A-15C, the implantable device 10 may include a docking member 30 extending from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10.

The head portion 32 may include a recess 82 extending into the head portion 32 from a proximal surface 84 of the head portion 32. The recess 82 may be configured to receive a rotational driving instrument therein. For example, the recess 82 may be configured to receive a distal driver mechanism of a rotational driving instrument therein. In some instances, the recess 82 may extend generally perpendicular to the longitudinal axis of the housing 12. In some embodiments, the recess 82 may extend across the head portion 32 from a first side of the head portion 32 to a second side of the head portion 32. As shown in FIG. 15C, the head portion 32 may include a distal surface 85 opposite the proximal surface 84 from which the neck portion 34 extends from. In some instances, the recess 82 may extend into the head portion 32 from the proximal surface 84 toward the distal surface 85, but does not extend to the distal surface 85. However, in other embodiments the recess 82 may extend to the distal surface 85.

The head portion 32 may also include a member 86 extending across the recess 82 dividing the recess 82 into a first recess portion 82a on a first side of the member 86 and a second recess portion 82b on a second side of the member 86. In some instances, the member 86 may extend generally perpendicular to the recess 82 and/or the longitudinal axis of the housing 12. As shown in FIGS. 15A-15C, in some instances the member 86 may be formed as a monolithic portion of the head portion 32 bridging across the recess 82. In other embodiments, however, the member 86 may be a separate component attached to the head portion 32.

A tether 80 may extend through a passage beneath the member 86 defined by the recess 82 during delivery of the implantable device 10. For example, the tether 80 may be attached to the member 86 and extend proximally from the member 86 along an elongate shaft of a delivery device to a location accessible by a physician during implantation of the implantable device 10. Once the implantable device 10 has been properly implanted in the heart H, the tether 80 may be detached from the member 86 and withdrawn from the patient.

Figure 16A:
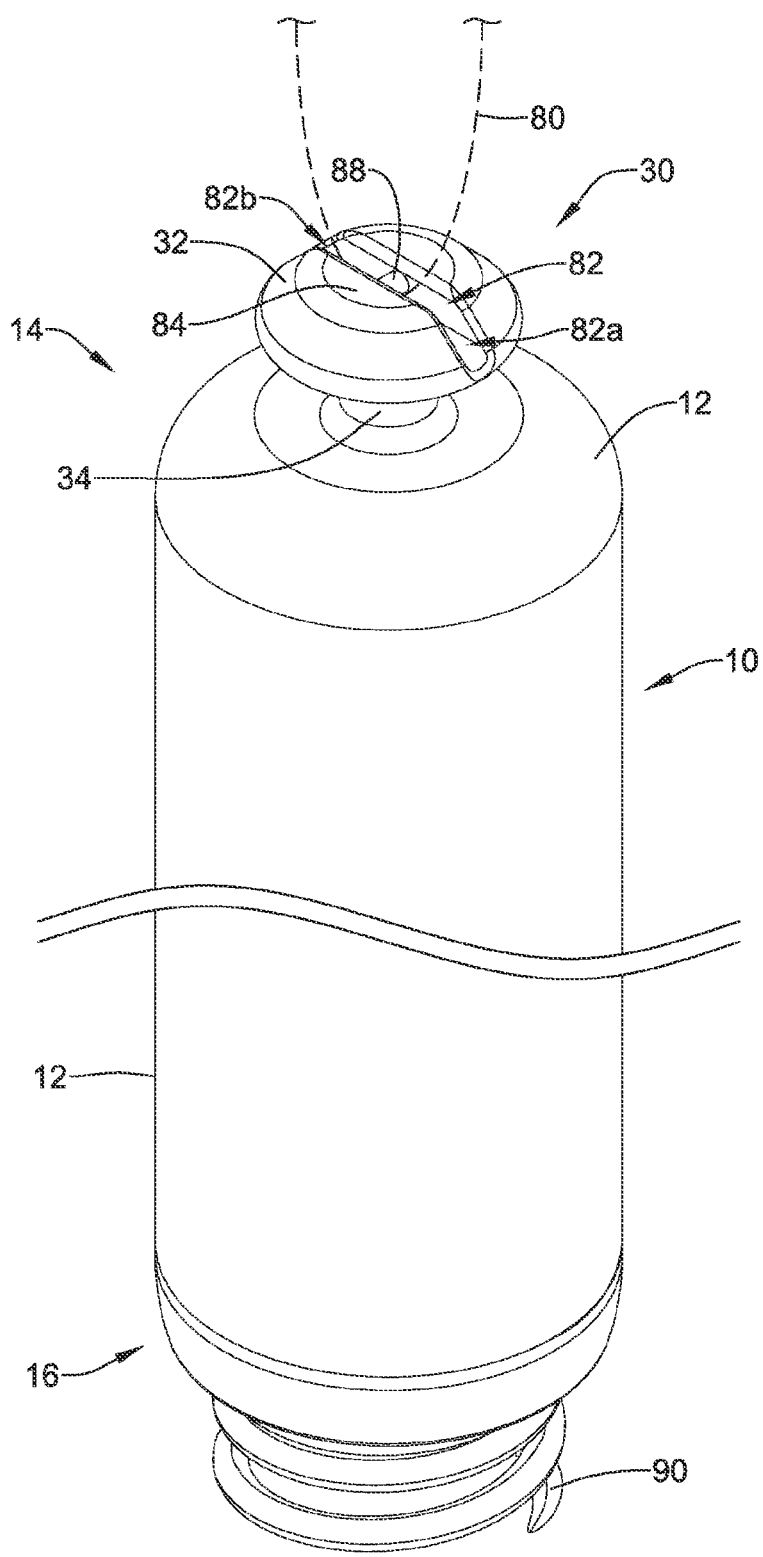
FIGS. 16A-16C illustrate another exemplary docking member of an implantable device.
Figure 16B:
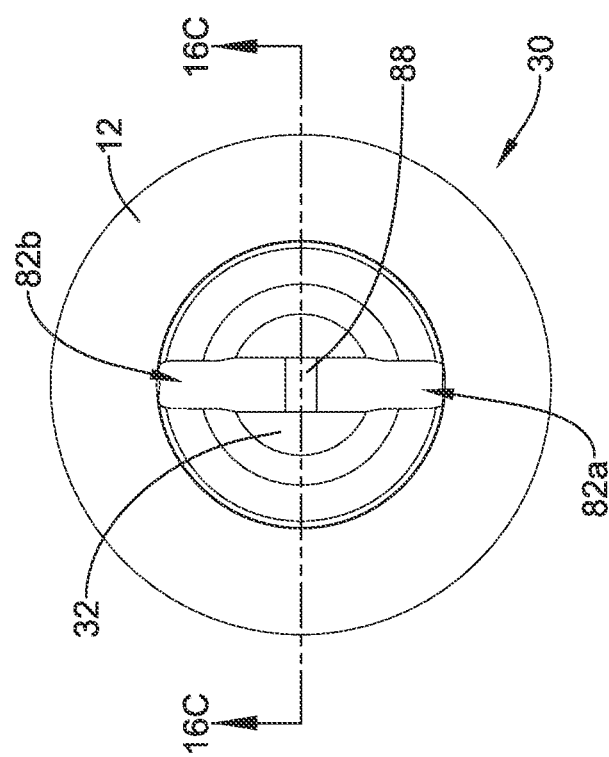
Figure 16C:
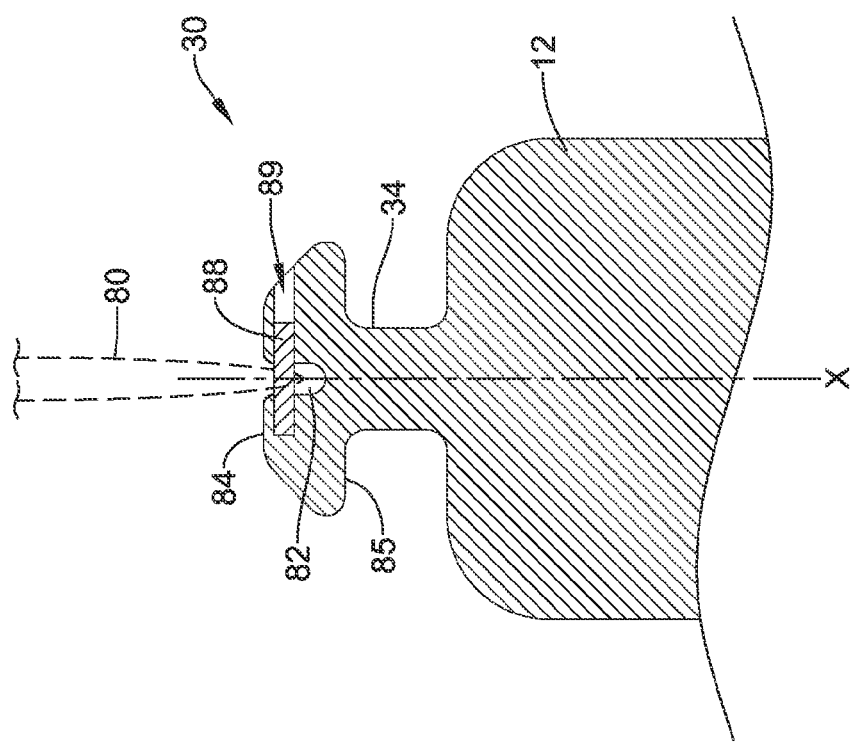

FIGS. 16A-16C illustrate another implantable device 10 including a helical fixation anchor 90 at the distal end 16 of the housing 12 configured to be screwed into a tissue wall through rotational motion of the implantable device 10 to anchor the implantable device 10 to the heart H. Similar to the embodiment of FIGS. 15A-15C, the docking member 30 may include an engagement feature configured to mate with an engagement feature of a delivery device to transfer rotational motion from a rotatable shaft of the delivery device to the implantable device 10.

For example, in the embodiment of FIGS. 16A-16C, the implantable device 10 may include a docking member 30 extending from the proximal end 14 of the housing 12 along a longitudinal axis of the housing 12. The docking member 30 may include a head portion 32 and a neck portion 34 extending between the housing 12 and the head portion 32. The head portion 32 may be an enlarged portion relative to the neck portion 34. For example, the head portion 32 may have a radial dimension from the longitudinal axis of the implantable device 10 which is greater than a radial dimension of the neck portion from the longitudinal axis of the implantable device 10.

The head portion 32 may include a recess 82 extending into the head portion 32 from a proximal surface 84 of the head portion 32. The recess 82 may be configured to receive a rotational driving instrument therein. For example, the recess 82 may be configured to receive a distal driver mechanism of a rotational driving instrument therein. In some instances, the recess 82 may extend generally perpendicular to the longitudinal axis of the housing 12. In some embodiments, the recess 82 may extend across the head portion 32 from a first side of the head portion 32 to a second side of the head portion 32. As shown in FIG. 16C, the head portion 32 may include a distal surface 85 opposite the proximal surface 84 from which the neck portion 34 extends from. In some instances, the recess 82 may extend into the head portion 32 from the proximal surface 84 toward the distal surface 85, but does not extend to the distal surface 85. However, in other embodiments the recess 82 may extend to the distal surface 85.

The head portion 32 may also include a member extending across the recess 82 dividing the recess 82 into a first recess portion 82a on a first side of the member and a second recess portion 82b on a second side of the member. As shown in FIGS. 16A-16C, the member may be a pin 88 extending across the recess 82 or bridging across the recess 82. In some instances, the pin 88 may extend generally perpendicular to the recess 82 and/or the longitudinal axis of the housing 12. The pin 88 may be inserted through a hole 89 in the head portion 32 to position the pin 88 across the recess 82, for example.

A tether 80 may extend through a passage beneath the pin 88 defined by the recess 82 during delivery of the implantable device 10. For example, the tether 80 may be attached to the pin 88 and extend proximally from the pin 88 along an elongate shaft of a delivery device to a location accessible by a physician during implantation of the implantable device 10. Once the implantable device 10 has been properly implanted in the heart H, the tether 80 may be detached from the pin 88 and withdrawn from the patient.

It is noted that in other embodiments the tether 80 may be attached to the docking member 30 (such as through a passage in the docking member 30) and extend proximally from the docking member 30 along an elongate shaft of a delivery device to a location accessible by a physician during implantation of the implantable device 10. Similarly, once the implantable device 10 has been properly implanted in the heart H, the tether 80 may be detached from the docking member 30 and withdrawn from the patient.

An exemplary delivery device 100 including a rotational driving instrument 102 and a delivery sheath 104 is illustrated in FIG. 17A. The rotational driving instrument 102 may include an elongate drive shaft 106 and a driver mechanism 108 at the distal end of the elongate drive shaft 106. The driver mechanism 108 may be configured for engagement with the head portion 32 of the docking member 30 to transfer rotational and/or longitudinal movement therebetween. The rotational driving instrument 102 may extend through a lumen 110 of the delivery sheath 104. The driving instrument 102 may be rotatable and longitudinally movable relative to the delivery sheath 104. The delivery sheath 104 may be sized such that the implantable device 10 may be positioned in a distal region of the lumen 110, with the driving instrument 102 engaged with a proximal portion of the implantable device 10 and extending proximally therefrom.

The driver mechanism 108 may include a pusher 112, such as a plate, located at the distal end of the elongate shaft 106 having a distal end surface 116 configured to engage the proximal surface 84 of the docking member 30. The driver mechanism 108 may also include one or more, or a plurality of protuberances, such as lugs 114, extending distally from the distal end surface 116 of the pusher 112, or otherwise arranged. For example, the driver mechanism 108 shown in FIG. 17A includes a first lug 114 and a second lug 114 spaced from the first lug 114 and extending in a distal direction from the distal end surface 116 of the pusher 112. The lug(s) 114 may be configured to engage in the recess 82 of the head portion 32 of the docking member 30.

The rotational driving instrument 102 may also include a lumen 118 extending therethrough. For example, the lumen 118 may extend through the elongate shaft 106 to an opening in the distal end surface 116 of the pusher 112 of the driver mechanism 108. The lumen 118 may be configured to receive the tether 80 therethrough such that the tether 80 may extend along the delivery device 100 to a proximal region of the delivery device 100 through the driving instrument 102. In other instances, the tether 80 may extend along the delivery device 100 through the lumen 110 of the delivery sheath 104 and external of the driving instrument 102, for example.

Figure 17B:
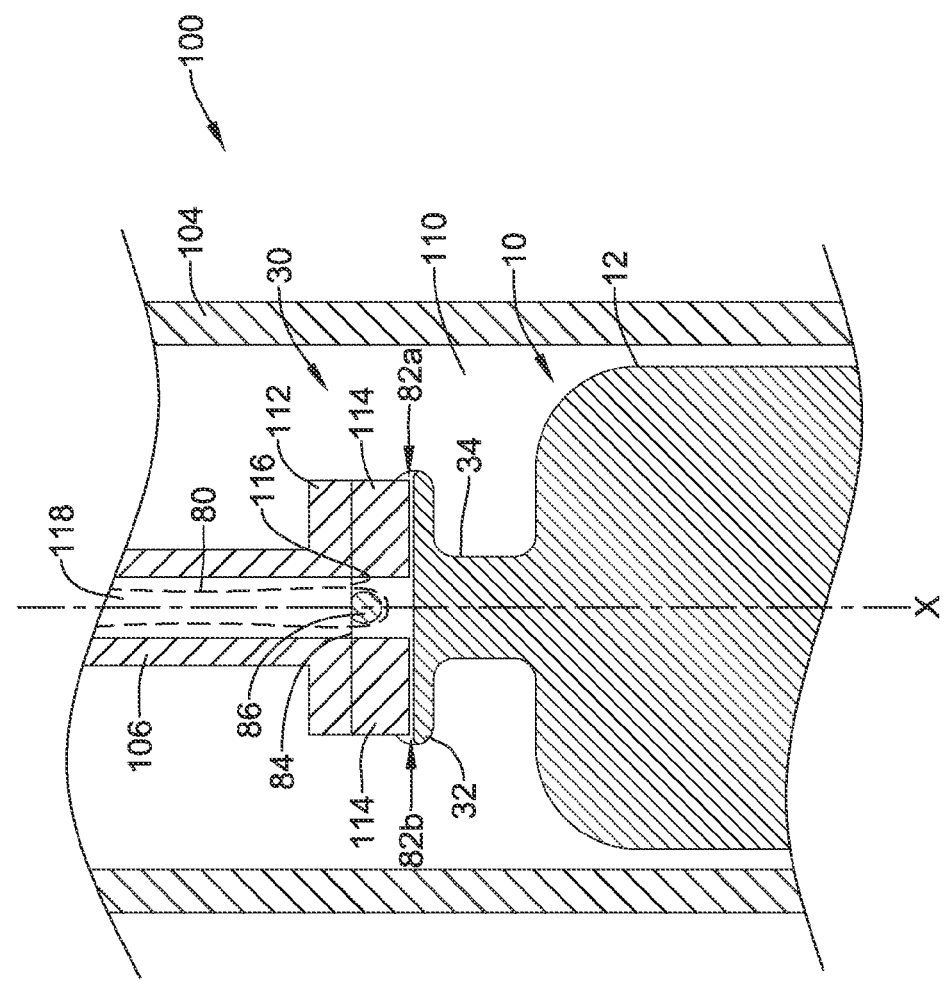
FIG. 17B illustrates the delivery device of FIG. 17A in engagement with the docking member of the implantable device of FIGS. 15A-15C.

FIG. 17B illustrates an exemplary interaction between the delivery device 100 and the implantable device 10 with the docking member 30 shown in FIGS. 15A-15C during delivery and implantation of the implantable device 10 in a heart H, or other desired anatomy. As shown in FIG. 17B, the implantable device 10 may be positioned in the lumen 110 of the delivery sheath 104 with the driving instrument 102 engaged with the docking member 30. For instance, the distal end surface 116 of the pusher 112 may abut the proximal surface 84 of the head portion 32 of the docking member 30 while the first lug 114 is positioned in the first recess portion 82a on a first side of the member 86 and the second lug 114 is positioned in the second recess portion 82b on a second side of the member 86.

Accordingly, with the driver mechanism 108 engaged to the docking member 30, rotational movement of the driving instrument 102 may be transferred to the implantable device 10 to screw the helical fixation anchor 90 into a tissue wall and/or unscrew the helical fixation anchor 90 from a tissue wall.

FIG. 17C illustrates an exemplary interaction between the delivery device 100 and the implantable device 10 with the docking member 30 shown in FIGS. 16A-16C during delivery and implantation of the implantable device 10 in a heart H, or other desired anatomy. In many respects the interaction may be similar to that described above regarding FIG. 17B. However, in FIG. 17C, the member extending across the recess 82 is shown as a pin 88. Accordingly, when the driver mechanism 108 is engaged to the docking member 30, the distal end surface 116 of the pusher 112 may abut the proximal surface 84 of the head portion 32 of the docking member 30 while the first lug 114 is positioned in the first recess portion 82a on a first side of the pin 88 and the second lug 114 is positioned in the second recess portion 82b on a second side of the pin 88.

Accordingly, with the driver mechanism 108 engaged to the docking member 30, rotational movement of the driving instrument 102 may be transferred to the implantable device 10 to screw the helical fixation anchor 90 into a tissue wall and/or unscrew the helical fixation anchor 90 from a tissue wall.

FIGS. 18A-18D illustrate alternative embodiments of a driver mechanism 108 for a rotational driving instrument 102 configured to mate with a docking member of an implantable device, such as one or more of the docking members 30 of the implantable device 10, described herein.

Figure 18A:
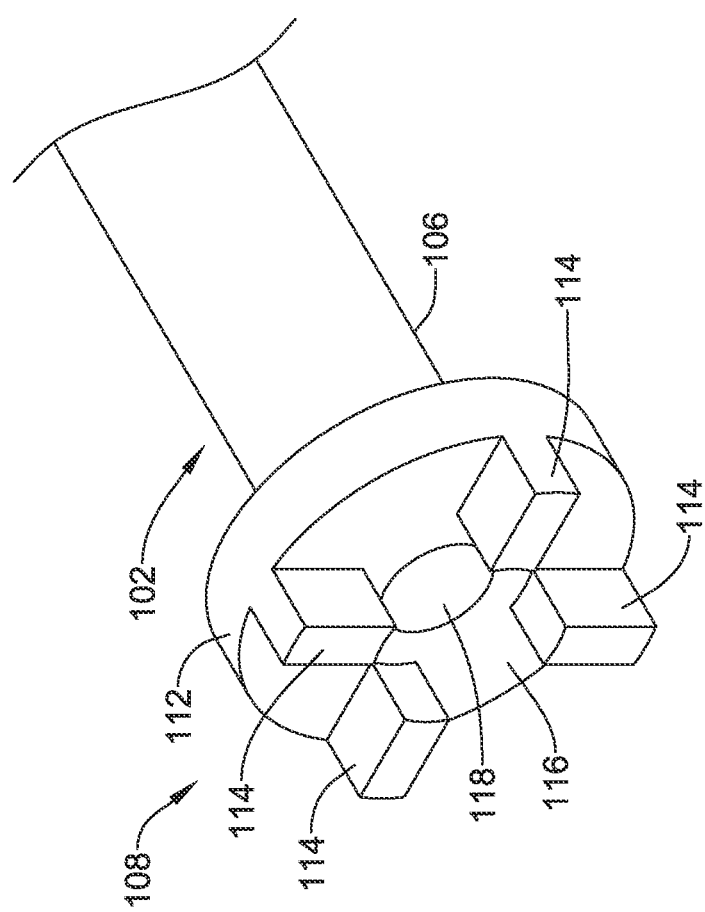
Figure 18B:
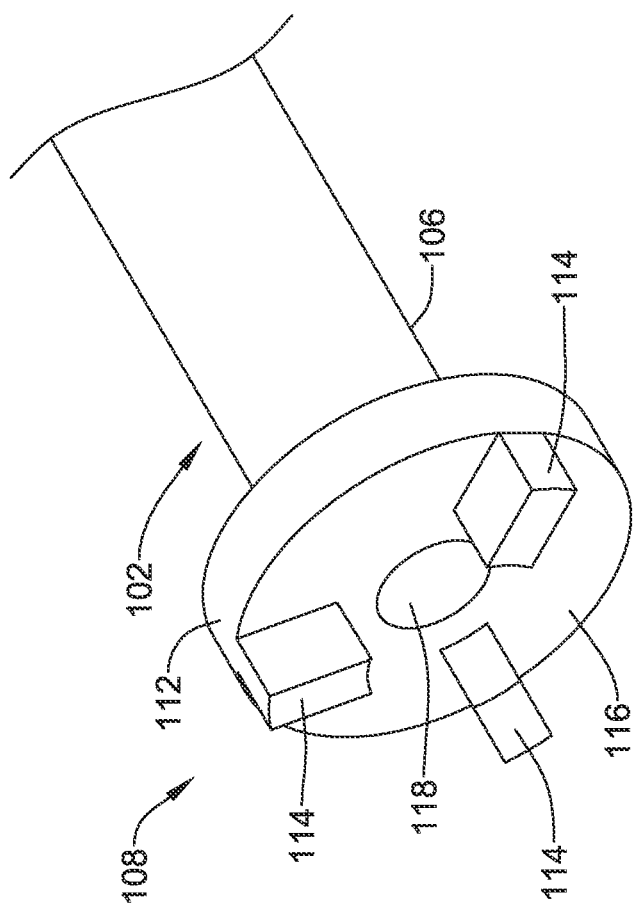
Figure 18C:
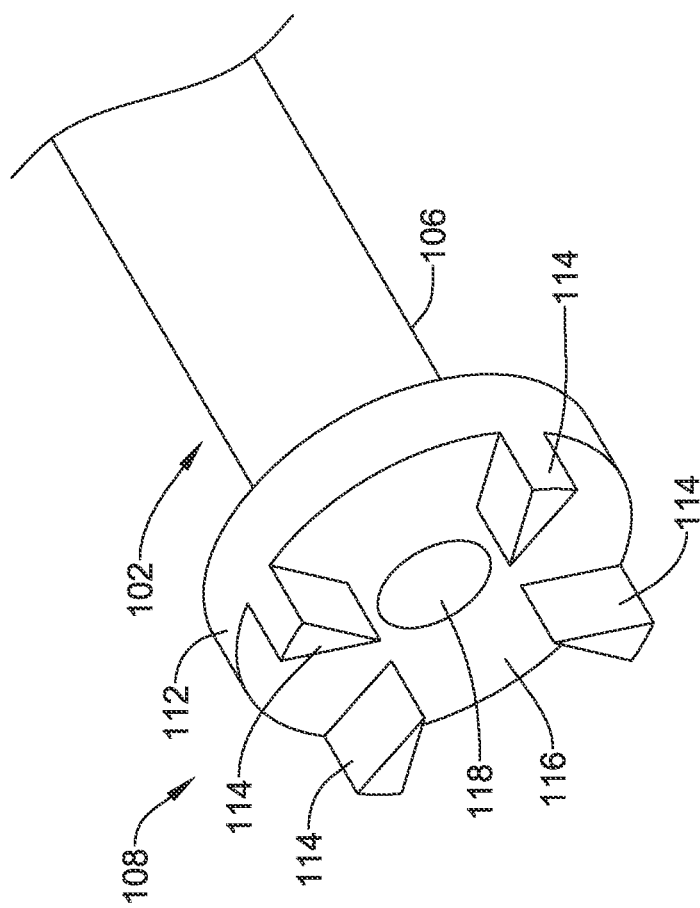

The driver mechanism 108 shown in FIGS. 18A-18C may be similar to the driver mechanism 108 shown in FIGS. 17A-17C. For example, the rotational driving instrument 102 may include an elongate drive shaft 106 and a driver mechanism 108 at the distal end of the elongate drive shaft 106. The driver mechanism 108 may be configured for engagement with the head portion 32 of the docking member 30 to transfer rotational and/or longitudinal movement therebetween. The rotational driving instrument 102 may extend through a lumen 110 of the delivery sheath 104 (shown in FIG. 17A).

The driver mechanism 108 may include a pusher 112 having a distal end surface 116 configured to engage the proximal surface 84 of the docking member 30 and one or more, or a plurality of protuberances, such as lugs 114, extending distally from the distal end surface 116 of the pusher 112. For example, the driver mechanism 108 shown in FIG. 18A includes four equally spaced apart lugs 114, the driver mechanism 108 shown in FIG. 18B includes three equally spaced apart lugs 114, and the driver mechanism 108 shown in FIG. 18C includes four equally spaced apart lugs 114 extending in a distal direction from the distal end surface 116 of the pusher 112. The lug(s) 114 may be configured to extend into openings between adjacent spokes 70 of the docking members 30 described herein, and engage in the spokes 70 of the head portion 32 of the docking member 30 to transfer rotational torque therebetween.

The rotational driving instrument 102 may also include a lumen 118 extending through the elongate shaft 106 configured to receive the tether 80 therethrough such that the tether 80 may extend along the delivery device 100 to a proximal region of the delivery device 100 through the driving instrument 102. In other instances, the tether 80 may extend along the delivery device 100 through the lumen 110 of the delivery sheath 104 and external of the driving instrument 102, for example.

The shape, size, quantity and arrangement of the lugs 114 may be chosen to complement and mate with the shape, size, quantity and arrangement of spokes 70 of the docking member 30. For example, the lugs 114 shown in FIG. 18C, may be triangular or wedge shaped to fit between adjacent spokes 70 of the docking member 30 shown in FIG. 8A, 9A, 10A or 14A. In other instances, the shape of the lugs 114 may be chosen to complement and mate with the spokes 70 shown in FIG. 11A, 12A or 13A, for example.

In other instances, as shown in FIG. 18D, the driver mechanism 108 of the rotational driving instrument 102 may include a socket 120 shaped, sized and configured to mate with the head portion 32 of the docking member 30 to transfer rotational torque therebetween. For example, as shown in FIG. 18D, the socket 120 may include opposing arcuate edges and opposing flat edges extending between the arcuate edges, configured to complement the shape and size of the docking member 30 shown in FIG. 4A. The flat edges of the socket 120 may engage the flat sides of the docking member 30 to transfer rotational torque therebetween. It is noted that in some instances, the socket 120 may include a single flat side for engagement with a flat side of the docking member 30.

In other instances, the socket 120 may have another shape, size and configuration to mate with the head portion 32 of another docking member 30. For example, the socket 120 may include a complementary shape, size and configuration to the head portion 32 of the docking member 30 shown in FIG. 8A, 9A, 10A, 11A, 12A, 13A or 14A such that the head portion 32 of the docking member 30 fits into the socket 120. The socket 120 may include at least one edge or surface configured to engage a surface of the head portion 32 of the docking member 30 to transfer rotational torque therebetween.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An implantable leadless cardiac pacing device comprising:
   a housing having a proximal end and a distal end;
   an electrode positioned proximate the distal end of the housing configured to be positioned adjacent cardiac tissue; and
   a docking member extending from the proximal end of the housing along a longitudinal axis of the housing, the docking member configured to facilitate retrieval of the implantable leadless cardiac pacing device;
   the docking member including a head portion and a neck portion extending between the housing and the head portion;
   the head portion having a radial dimension from the longitudinal axis and the neck portion having a radial dimension from the longitudinal axis less than the radial dimension of the head portion;
   the head portion including a plurality of radially extending spokes extending radially outward from the longitudinal axis of the housing;
   wherein each spoke includes a base portion proximate the longitudinal axis of the housing and a free end extending radially outward from the base portion, wherein a width of each spoke increases from the base portion toward the free end of the spoke.

2. The implantable leadless cardiac pacing device of claim 1, wherein each of the spokes extends at an oblique angle to the longitudinal axis of the housing toward the distal end such that the free ends of the plurality of spokes are positioned closer to the distal end of the housing than the base portion of the spokes proximate the longitudinal axis of the housing.

3. The implantable leadless cardiac pacing device of claim 1, wherein the plurality of spokes are configured to mate with an engagement mechanism of a rotational driving instrument to transfer rotational torque to the implantable leadless cardiac pacing device.

4. An implantable leadless cardiac pacing device comprising:
   a housing having a proximal end and a distal end;
   an electrode positioned proximate the distal end of the housing configured to be positioned adjacent cardiac tissue; and
   a docking member extending from the proximal end of the housing along a longitudinal axis of the housing, the docking member configured to facilitate retrieval of the implantable leadless cardiac pacing device;
   the docking member including a head portion and a neck portion extending between the housing and the head portion;
   the head portion having a radial dimension from the longitudinal axis and the neck portion having a radial dimension from the longitudinal axis less than the radial dimension of the head portion;
   the head portion including a plurality of radially extending spokes extending radially outward from the longitudinal axis of the housing;
   wherein each of the spokes includes a body portion extending radially outward to a free end of the spoke and a crossing member extending transverse to the body portion.

5. The implantable leadless cardiac pacing device of claim 4, wherein the crossing member extends in opposite directions from the body portion.

6. The implantable leadless cardiac pacing device of claim 5, wherein the spoke is T-shaped.

7. The implantable leadless cardiac pacing device of claim 5, wherein each spoke includes undercut portions at a junction between the crossing member and the body portion of the spoke.

8. A system for retrieving an implantable leadless cardiac pacing device, comprising:
   an implantable cardiac pacing device having a housing having a longitudinal axis, an electrode positioned proximate a distal end of the housing, and a docking member extending from a proximal end of the housing opposite the distal end, the docking member including a head portion and a neck portion extending between the housing and the head portion, the head portion including a plurality of radially extending spokes extending radially outward from the longitudinal axis of the housing; and
   a retrieval device including a snare having an elongate shaft and one or more loops at a distal end of the elongate shaft;
   wherein the one or more loops of the retrieval device are capable of encircling one or more of the radially extending spokes to capture the docking member with the snare;
   wherein each spoke includes:
   i) a base portion proximate the longitudinal axis of the housing and a free end extending radially outward from the base portion, wherein a width of each spoke increases from the base portion toward the free end of the spoke; or
   ii) a body portion extending radially outward to a free end of the spoke and a crossing member extending transverse to the body portion.

9. The system of claim 8, wherein if the spoke includes ii), the crossing member extends in opposite directions from the body portion.

10. The system of claim 9, wherein the spoke is T-shaped.

11. The system of claim 9, wherein each spoke includes undercut portions at a junction between the crossing member and the body portion of the spoke.

12. The system of claim 8, wherein if the spoke includes i), each of the spokes extends at an oblique angle to the longitudinal axis of the housing toward the distal end such that the free ends of the plurality of spokes are positioned closer to the distal end of the housing than the base portion of the spokes proximate the longitudinal axis of the housing.

* * * * *